(12) United States Patent
Abraham et al.

(10) Patent No.: US 9,493,557 B2
(45) Date of Patent: Nov. 15, 2016

(54) CHEMOKINE BINDING POLYPEPTIDES FOR TREATING AUTOIMMUNITY AND INFLAMMATION

(71) Applicant: Biokine Therapeutics Ltd., Nes Ziona (IL)

(72) Inventors: Michal Abraham, Mevasseret Zion (IL); Orly Eizenberg, Rechovot (IL); Amnon Peled, Tel-Aviv (IL)

(73) Assignee: Biokine Therapeutics Ltd., Nes Ziona (IL)

( * ) Notice: Subject to any disclaimer, the term of this patent is extended or adjusted under 35 U.S.C. 154(b) by 0 days.

(21) Appl. No.: 14/178,301

(22) Filed: Feb. 12, 2014

(65) Prior Publication Data

US 2014/0154249 A1    Jun. 5, 2014

Related U.S. Application Data

(62) Division of application No. 13/378,063, filed as application No. PCT/IL2010/000473 on Jun. 15, 2010, now Pat. No. 8,685,398.

(60) Provisional application No. 61/213,493, filed on Jun. 15, 2009.

(51) Int. Cl.
| | | |
|---|---|---|
| *C07K 14/52* | (2006.01) | |
| *C07K 7/06* | (2006.01) | |
| *C07K 16/24* | (2006.01) | |
| *A61K 47/48* | (2006.01) | |
| *C07K 7/08* | (2006.01) | |
| *C07K 14/715* | (2006.01) | |
| *A61K 38/19* | (2006.01) | |

(52) U.S. Cl.
CPC ......... *C07K 16/24* (2013.01); *A61K 47/48246* (2013.01); *A61K 47/48423* (2013.01); *A61K 47/48507* (2013.01); *C07K 7/06* (2013.01); *C07K 7/08* (2013.01); *C07K 14/7158* (2013.01); *A61K 38/195* (2013.01); *C07K 2319/30* (2013.01)

(58) Field of Classification Search
None
See application file for complete search history.

(56) References Cited

U.S. PATENT DOCUMENTS

| 5,116,964 A | 5/1992 | Capon et al. |
|---|---|---|
| 2012/0087921 A1 | 4/2012 | Abraham et al. |

FOREIGN PATENT DOCUMENTS

| JP | 2003-512011 | 4/2003 |
|---|---|---|
| WO | WO 00/24782 | 5/2000 |
| WO | WO 03/072599 | 9/2003 |
| WO | WO 2007/052173 | 5/2007 |
| WO | WO 2007/094005 | 8/2007 |
| WO | WO 2010/146584 | 12/2010 |

OTHER PUBLICATIONS http://www.stedmansonline.com/index.aspx ; Systemic lupus erythematosus; Jun. 23, 2015.*
http://www.stedmansonline.com/index.aspx; Myasthenia gravis, Jun. 23, 2015.*
http://www.stedmansonline.com/index.aspx; Allograft rejection; Jun. 23, 2015.*
http://www.stedmansonline.com/index.aspx; Malignant; Jun. 23, 2015.*
Advisory Action Before the Filing of an Appeal Brief Dated Sep. 23, 2013 From the US Patent and Trademark Office Re. U.S. Appl. No. 13/378,063.
Communication Pursuant to Article 94(3) EPC Dated Dec. 14, 2012 From the European Patent Office Re. Application No. 10735337.7.
International Preliminary Report on Patentability Dated Dec. 29, 2011 From the International Bureau of WIPO Re. Application No. PCT/IL2010/000473.
International Search Report and the Written Opinion Dated Oct. 22, 2010 From the International Searching Authority Re. Application No. PCT/IL2010/000473.
Notice of Allowance Dated Oct. 29, 2013 From the US Patent and Trademark Office Re. U.S. Appl. No. 13/378,063.
Notification of Office Action Dated Oct. 31, 2013 From the State Intellectual Property Office of the People's Republic of China Re. Application No. 201080036127.9 and Its Translation Into English.
Office Action Dated Jul. 8, 2013 From the Israel Patent Office Re. Application No. 216978 and Its Translation Into English.
Official Action Dated Jul. 1, 2013 From the US Patent and Trademark Office Re. U.S. Appl. No. 13/378,063. Official Action Dated Jan. 8, 2013 From the US Patent and Trademark Office Re. U.S. Appl. No. 13/378,063.
Restriction Official Action Dated Aug. 23, 2012 From the US Patent and Trademark Office Re. U.S. Appl. No. 13/378,063.
Translation of Office Action Dated May 2, 2013 From the State Intellectual Property Office of the People's Republic of China Re. Application No. 201080036127.9.
Translation of Search Report May 2, 2013 From the State Intellectual Property Office of the People's Republic of China Re. Application No. 201080036127.9.
Bork "Powers and Pitfalls in Sequence Analysis: The 70% Hurdle", Genome Research, 10: 398-400, 2000.
Doercks et al. "Protein Annotation: Detective Work for Function Prediction", Trends in Genetics, TiG, 14(6): 248-250, Jun. 1998.
Skolnick et al. "From Genes to Protein Structure and Function: Novel Applications of Computational Approaches in the Genomic Era", Trends in Biotechnology, TiBTech, 18(1): 34-39, Jan. 2000.
Tokuriki et al. "Stability Effects of Mutations and Protein Evolvability", Current Opinion in Structural Biology, 19: 596-604, 2009.
Wells "Additivity of Mutational Effects in Proteins", Biochemistry, 29(37): 8509-8517, Sep. 18, 1990.
Examination Report Dated Feb. 18, 2014 From the Instituto Mexicano de la Propiedad Industrial Re. Application No. MX/a/2011/013457 and Its Translation Into English.

(Continued)

*Primary Examiner* — Bridget E Bunner
*Assistant Examiner* — Fozia Hamud

(57) ABSTRACT

Novel polypeptides comprising a chemokine-binding peptide and an Fc fragment are disclosed. The polypeptides are capable of binding to certain chemokines so as to modulate their activity. These polypeptides can be used to modulate in vivo chemokine-dependent processes such as inflammation and autoimmunity, and to treat associated conditions.

2 Claims, 9 Drawing Sheets

(56) References Cited

OTHER PUBLICATIONS

Office Action Dated Mar. 26, 2015 From the Israel Patent Office Re. Application No. 216978 and Its Translation Into English.
Communication Pursuant to Article 94(3) EPC Dated May 7, 2014 From the European Patent Office Re. Application No. 10735337.7.
Notice of Reason for Rejection Dated Oct. 17, 2014 From the Japanese Patent Office Re. Application No. 2012-515627 and Its Translation Into English.
Kasuga et al. "Sensitization of Human Glioblastomas to Tumor Necrosis Factor-Related Apoptosis-Inducing Ligand (TRAIL) by NF-KB Inhibitors", Cancer Science, 95(10): 840-844, Oct. 2004.
Toyooka et al. "CD28 Co-Stimulatory Signals Induce IL-2 Receptor Expression on antigen-Stimulated Virgin T Cells by An 1L-2-Independent Mechanism", International Immunology, 8(2): 159-169, Feb. 1996.
Duan et al. "Inhaled P38[Alpha] Mitogen-Activated Protein Kinase Antisense Oligonucleotide Attenuates Asthma in Mice", American Journal of Respiratory and Critical Care Medicine, 171: 571-578, Originally Published Nov. 19, 2004.
Escott et al. "Effect of the P38 Kinase Inhibitor, SB 203580, on Allergic Airway Inflammation in the Rat", British Journal of Pharmacology, 131(2): 173-176, Sep. 2000.
Haddad et al. "Role of P38 MAP Kinase in LPS-Induced Airway Inflammation in the Rat", British Journal of Pharmacology, 132(8): 1715-1724, Apr. 2001.
Underwood et al. "SB 239063, A P38 MAPK Inhibitor, Reduces Neutrophilia, Inflammatory Cytokines, MMP-9, and Fibrosis in Lung", American Journal of Physiology, Lung Cellular and Molecular Physiology, 279(5): L895-L902, Nov. 2000.
Underwood et al. "SB 239063, A Potent P38 MAP Kinase Inhibitor, Reduces Inflammatory Cytokine Production, Airways Eosinophil Infiltration, and Persistence", The Journal of Pharmacology and Experimental Therapeutics, 293(1): 281-288, Apr. 2000.
Baggiolini et al. "CC Chemokines in Allergic Inflammation", Immunology Today, 15(3): 127-133, 1994.
Cocchi et al. "Identification of Rantes, MIP-1[Alpha], and MIP-1[Beta] as the Major HIV-Suppressive Factors Produced by CD8+ T Cells", Science, 270(5243): 1811-1815, Dec. 15, 1995.
Epifano et al. "Auraptene and Its Effects on the Re-Emergence of Colon Cancer Stem Cells", Phytotherapy Research, 27(5): 784-786, Epub Jul. 4, 2012.
Huang et al. "Anticancer Activities of Polyynes From the Root Bark of Oplopanax Horridus and Their Acetylated Derivatives", Molecules, 19: 6142-6162, May 14, 2014.
Kioi et al. "Inhibition of Vasculogenesis, But Not Angiogenesis, Prevents the Recurrence of Glioblastoma After Irradiation in Mice", the Journal of Clincal Investigation, 120(3): 694-705, Mar. 2010.
Kryczek et al. "Stroma-Derived Factor (SDF-1/CXCL12) and Human Tumor Pathogenesis", American Journal of Physioloy, Cell Physiology, 292(3): C987-C995, First Published Aug. 30, 2006.
Ma et al. "Impaired B-Lymphopoiesis, Myelopoiesis, and Derailed Cerebellar Neuron Migration in CXCR4- and SDF-1-Deficient Mice", Proc. Natl. Acad. Sci. USA, 95(16): 9448-9453, Aug. 1998.
Nomura et al. "The Antibacterial Activity of Compounds Isolated From Oakmoss Against *Legionella pneumophila* and Other *Legionella* Spp.", Biological & Pharmaceutical Bulletin, 35(9): 1560-1567, 2012.
Smith et al. "CXCR4 Regulates Growth of Both Primary and Metastatic Breast Cancer", Cancer Research, 64: 8604-8612, Dec. 1, 2004.
Strieter et al. "The Functional Role of the ELR Motif in CXC Chemokine-Mediated Angiogenesis", The Journal of Biological Chemistry, 270(45): 27348-27357, Nov. 10, 1995.
Vaddi et al. "Regulation of Monocyte Integrin Expression by Beta-Family Chemokines", The Journal of Immunology, 153(10): 4721-4732, Nov. 15, 1994.
Wang et al. "Identification of Potential Anticancer Compounds From Oplopanax Hoiridus", Phytomedicine, 20(11): 999-1006, Aug. 15, 2013.
Wilson et al. "CXCR4 Signaling Mediates Morphine-Induced Tactile Hyperalgesia", Brain, Behavior, and Immunity, 25(3): 565-573, Epub Dec. 28, 2010.
Zheng et al. "Migration of Endothelial Progenitor Cells Mediated by Stromal Cell-Derived Factor-1[Alpha]/CXCR4 Via P13K/Akt/eNOS Signal Transduction Pathway", Journal of Cardiovascular Pharmacology, 50(3): 274-280, Sep. 2007.
International Search Report and the Written Opinion Dated Mar. 28, 2016 From the International Searching Authority Re. Application No. PCT/IL2015/051190.
Rutar et al. "Small Interfering RNA-Mediated Suppression of Cc12 in Mueller Cells Attenuates Microglial Recruitment and Photoreceptor Death Following Retinal Degeneration", Journal of Neuroinflammation, 9(221): 1-15, Published Online Sep. 19, 2012.
Wallace et al. "The Role of Chemokines and Their Receptors in Ocular Disease", Progress in Retinal and Eye Research, 23(4): 435-448, Jul. 2004. p. 446, Pont No. 10.
Luhmann et al. The Relevance of Chemokine Signalling in Modulating Inherited and Age-Related Retinal Degenerations:, Retinal Degenerative Diseases, Chap.54: 427-433, Mar. 25, 2014.

* cited by examiner

SEQUENCE LISTING

<160> NUMBER OF SEQ ID NOS: 174

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Cys Ala His Leu Ser Pro His Lys Cys
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic peptide

<400> SEQUENCE: 2

Cys Asp Ile Pro Trp Arg Asn Glu Cys
1               5

```
<210> SEQ ID NO 3
<211> LENGTH: 9
<212> TYPE: PRT
<213> ORGANISM: Artificial sequence
<220> FEATURE:
<223> OTHER INFORMATION: Synthetic peptide

<400> SEQUENCE: 3

Cys Asp Pro Leu Arg Gln His Ser Cys
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptide

<400> SEQUENCE: 4

Cys Asp Ser Leu Gly His Trp Leu Cys
1               5

<210> SEQ ID NO 5
<211> LENGTH: 9
<212> TYPE: PRT
<213> ORGANISM: Artificial sequence
<220> FEATURE:
<223> OTHER INFORMATION: Synthetic peptide

<400> SEQUENCE: 5

Cys Asp Tyr Thr Thr Arg His Ser Cys
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic peptide

<400> SEQUENCE: 6

Cys His Gly Thr Leu Asn Pro Glu Cys
1               5

<210> SEQ ID NO 7
<211> LENGTH: 9
<212> TYPE: PRT
<213> ORGANISM: Artificial sequence
<220> FEATURE:
<223> OTHER INFORMATION: Synthetic peptide

<400> SEQUENCE: 7

Cys His His Asn Leu Ser Trp Glu Cys
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic peptide

<400> SEQUENCE: 8

Cys His Ile Trp Thr Leu Ala Ser Cys
1               5

<210> SEQ ID NO 9
```

```
<211> LENGTH: 9
<212> TYPE: PRT
<213> ORGANISM: Artificial sequence
<220> FEATURE:
<223> OTHER INFORMATION: Synthetic peptide

<400> SEQUENCE: 9

Cys His Asn Thr Phe Ser Pro Arg Cys
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic peptide

<400> SEQUENCE: 10

Cys Ile Pro Leu His Ala Ser Leu Cys
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic peptide

<400> SEQUENCE: 11

Cys Ile Thr Thr Thr Ser Leu Ser Cys
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic peptide

<400> SEQUENCE: 12

Cys Lys Leu Thr Thr Cys Lys Asp Cys
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic peptide

<400> SEQUENCE: 13

Cys Lys Asn His Thr Thr Phe Trp Cys
1               5

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

Cys Leu Lys Leu Leu Ser Arg Ser Cys
1               5

<210> SEQ ID NO 15
<211> LENGTH: 9
```

```
<212> TYPE: PRT
<213> ORGANISM: Artificial sequence
<220> FEATURE:
<223> OTHER INFORMATION: Synthetic peptide

<400> SEQUENCE: 15

Cys Leu Leu Lys Ala His Pro Ser Cys
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic peptide

<400> SEQUENCE: 16

Cys Leu Asn Gln Leu Lys Gln Ala Cys
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic peptide

<400> SEQUENCE: 17

Cys Met Asn Phe Pro Ser Pro His Cys
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic peptide

<400> SEQUENCE: 18

Cys Pro Gln Ser Pro Thr Tyr Thr Cys
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic peptide

<400> SEQUENCE: 19

Cys Pro Ser Ser Ala Ile His Thr Cys
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic peptide

<400> SEQUENCE: 20

Cys Pro Thr Ser Thr Ala Arg Ile Cys
1               5

<210> SEQ ID NO 21
<211> LENGTH: 9
<212> TYPE: PRT
```

```
<213> ORGANISM: Artificial sequence
<220> FEATURE:
<223> OTHER INFORMATION: Synthetic peptide

<400> SEQUENCE: 21

Cys Gln Ala Ser Ser Phe Pro Ser Cys
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic peptide

<400> SEQUENCE: 22

Cys Gln Pro Tyr Phe Trp Tyr Arg Cys
1               5

<210> SEQ ID NO 23
<211> LENGTH: 9
<212> TYPE: PRT
<213> ORGANISM: Artificial sequence
<220> FEATURE:
<223> OTHER INFORMATION: Synthetic peptide

<400> SEQUENCE: 23

Cys Gln Thr Leu Thr Pro Ser Ile Cys
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic peptide

<400> SEQUENCE: 24

Cys Ser Lys Leu Gly His Leu Trp Cys
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Any amino acid

<400> SEQUENCE: 25

Cys Ser Lys Thr Pro Glu Arg Ile Xaa
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic peptide

<400> SEQUENCE: 26

Cys Ser Asn Asn Asn Arg Met Thr Cys
1               5
```

```
<210> SEQ ID NO 27
<211> LENGTH: 9
<212> TYPE: PRT
<213> ORGANISM: Artificial sequence
<220> FEATURE:
<223> OTHER INFORMATION: Synthetic peptide

<400> SEQUENCE: 27

Cys Ser Pro Ile Leu Ser Leu Ser Cys
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic peptide

<400> SEQUENCE: 28

Cys Ser Pro Thr Asn Phe Thr Arg Cys
1               5

<210> SEQ ID NO 29
<211> LENGTH: 9
<212> TYPE: PRT
<213> ORGANISM: Artificial sequence
<220> FEATURE:
<223> OTHER INFORMATION: Synthetic peptide

<400> SEQUENCE: 29

Cys Ser Arg Pro Ala Met Asn Val Cys
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic peptide

<400> SEQUENCE: 30

Cys Ser Thr Lys Ala Tyr Pro Asn Cys
1               5

<210> SEQ ID NO 31
<211> LENGTH: 9
<212> TYPE: PRT
<213> ORGANISM: Artificial sequence
<220> FEATURE:
<223> OTHER INFORMATION: Synthetic peptide

<400> SEQUENCE: 31

Cys Ser Thr Ser Ser Cys Gly Ser Cys
1               5

<210> SEQ ID NO 32
<211> LENGTH: 9
<212> TYPE: PRT
<213> ORGANISM: Artificial sequence
<220> FEATURE:
<223> OTHER INFORMATION: Synthetic peptide

<400> SEQUENCE: 32

Cys Ser Tyr Trp Gly His Arg Asp Cys
1               5

<210> SEQ ID NO 33
```

```
<211> LENGTH: 9
<212> TYPE: PRT
<213> ORGANISM: Artificial sequence
<220> FEATURE:
<223> OTHER INFORMATION: Synthetic peptide

<400> SEQUENCE: 33

Cys Thr Ala His Asp Ala Asn Ala Cys
1               5

<210> SEQ ID NO 34
<211> LENGTH: 9
<212> TYPE: PRT
<213> ORGANISM: Artificial sequence
<220> FEATURE:
<223> OTHER INFORMATION: Synthetic peptide

<400> SEQUENCE: 34

Cys Thr Ala Asn Ser Glu Lys Thr Cys
1               5

<210> SEQ ID NO 35
<211> LENGTH: 9
<212> TYPE: PRT
<213> ORGANISM: Artificial sequence
<220> FEATURE:
<223> OTHER INFORMATION: Synthetic peptide

<400> SEQUENCE: 35

Cys Thr His Pro Lys Ala Ser Met Cys
1               5

<210> SEQ ID NO 36
<211> LENGTH: 9
<212> TYPE: PRT
<213> ORGANISM: Artificial sequence
<220> FEATURE:
<223> OTHER INFORMATION: Synthetic peptide

<400> SEQUENCE: 36

Cys Thr Lys Thr Ile Asn Gly Lys Cys
1               5

<210> SEQ ID NO 37
<211> LENGTH: 9
<212> TYPE: PRT
<213> ORGANISM: Artificial sequence
<220> FEATURE:
<223> OTHER INFORMATION: Synthetic peptide

<400> SEQUENCE: 37

Cys Thr Asn Met Gln Ser Pro Leu Cys
1               5

<210> SEQ ID NO 38
<211> LENGTH: 9
<212> TYPE: PRT
<213> ORGANISM: Artificial sequence
<220> FEATURE:
<223> OTHER INFORMATION: Synthetic peptide

<400> SEQUENCE: 38

Cys Thr Pro Phe Thr Lys Leu Pro Cys
1               5

<210> SEQ ID NO 39
<211> LENGTH: 9
```

```
<212> TYPE: PRT
<213> ORGANISM: Artificial sequence
<220> FEATURE:
<223> OTHER INFORMATION: Synthetic peptide

<400> SEQUENCE: 39

Cys Thr Pro Thr Thr Asp Ser Ile Cys
1               5

<210> SEQ ID NO 40
<211> LENGTH: 9
<212> TYPE: PRT
<213> ORGANISM: Artificial sequence
<220> FEATURE:
<223> OTHER INFORMATION: Synthetic peptide

<400> SEQUENCE: 40

Cys Thr Gln Gln Asn Gly His Pro Cys
1               5

<210> SEQ ID NO 41
<211> LENGTH: 10
<212> TYPE: PRT
<213> ORGANISM: Artificial sequence
<220> FEATURE:
<223> OTHER INFORMATION: Synthetic peptide

<400> SEQUENCE: 41

Ala Cys Thr Thr Pro Ser Lys His Gln Cys
1               5                   10

<210> SEQ ID NO 42
<211> LENGTH: 9
<212> TYPE: PRT
<213> ORGANISM: Artificial sequence
<220> FEATURE:
<223> OTHER INFORMATION: Synthetic peptide

<400> SEQUENCE: 42

Cys Thr Tyr Asn Val Ala Lys Pro Cys
1               5

<210> SEQ ID NO 43
<211> LENGTH: 10
<212> TYPE: PRT
<213> ORGANISM: Artificial sequence
<220> FEATURE:
<223> OTHER INFORMATION: Synthetic peptide

<400> SEQUENCE: 43

Ala Cys Ala Pro Leu Met Phe Ser Gln Cys
1               5                   10

<210> SEQ ID NO 44
<211> LENGTH: 10
<212> TYPE: PRT
<213> ORGANISM: Artificial sequence
<220> FEATURE:
<223> OTHER INFORMATION: Synthetic peptide

<400> SEQUENCE: 44

Ala Cys His Ala Ser Leu Lys His Arg Cys
1               5                   10

<210> SEQ ID NO 45
<211> LENGTH: 11
<212> TYPE: PRT
```

<213> ORGANISM: Artificial sequence
<220> FEATURE:
<223> OTHER INFORMATION: Synthetic peptide

<400> SEQUENCE: 45

Ala His Phe Ser Pro Asn Leu Leu Leu Gly Gly
1               5                   10

<210> SEQ ID NO 46
<211> LENGTH: 12
<212> TYPE: PRT
<213> ORGANISM: Artificial sequence
<220> FEATURE:
<223> OTHER INFORMATION: Synthetic peptide

<400> SEQUENCE: 46

Ala His Ser Leu Lys Ser Ile Thr Asn His Gly Leu
1               5                   10

<210> SEQ ID NO 47
<211> LENGTH: 12
<212> TYPE: PRT
<213> ORGANISM: Artificial sequence
<220> FEATURE:
<223> OTHER INFORMATION: Synthetic peptide

<400> SEQUENCE: 47

Ala Lys Thr Leu Met Pro Ser Pro Phe Pro Arg Thr
1               5                   10

<210> SEQ ID NO 48
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (12)..(12)
<223> OTHER INFORMATION: Gln, Leu or Gly

<400> SEQUENCE: 48

Ala Ser Ala Val Gly Ser Leu Ser Ile Arg Trp Xaa
1               5                   10

<210> SEQ ID NO 49
<211> LENGTH: 12
<212> TYPE: PRT
<213> ORGANISM: Artificial sequence
<220> FEATURE:
<223> OTHER INFORMATION: Synthetic peptide

<400> SEQUENCE: 49

Ala Ser Trp Val Asp Ser Arg Gln Pro Ser Ala Ala
1               5                   10

<210> SEQ ID NO 50
<211> LENGTH: 11
<212> TYPE: PRT
<213> ORGANISM: Artificial sequence
<220> FEATURE:
<223> OTHER INFORMATION: Synthetic peptide

<400> SEQUENCE: 50

Cys Pro Gln Leu Thr Val Gly Gln His Arg Thr
1               5                   10

```
<210> SEQ ID NO 51
<211> LENGTH: 12
<212> TYPE: PRT
<213> ORGANISM: Artificial sequence
<220> FEATURE:
<223> OTHER INFORMATION: Synthetic peptide

<400> SEQUENCE: 51

Asp Leu Pro Pro Thr Leu His Thr Thr Gly Ser Pro
1               5                   10

<210> SEQ ID NO 52
<211> LENGTH: 12
<212> TYPE: PRT
<213> ORGANISM: Artificial sequence
<220> FEATURE:
<223> OTHER INFORMATION: Synthetic peptide

<400> SEQUENCE: 52

Asp Ser Ser Asn Pro Ile Phe Trp Arg Pro Ser Ser
1               5                   10

<210> SEQ ID NO 53
<211> LENGTH: 12
<212> TYPE: PRT
<213> ORGANISM: Artificial sequence
<220> FEATURE:
<223> OTHER INFORMATION: Synthetic peptide

<400> SEQUENCE: 53

Glu Phe Leu Gly Val Pro Ala Ser Leu Val Asn Pro
1               5                   10

<210> SEQ ID NO 54
<211> LENGTH: 12
<212> TYPE: PRT
<213> ORGANISM: Artificial sequence
<220> FEATURE:
<223> OTHER INFORMATION: Synthetic peptide

<400> SEQUENCE: 54

Glu Ser Asp Leu Thr His Ala Leu His Trp Leu Gly
1               5                   10

<210> SEQ ID NO 55
<211> LENGTH: 12
<212> TYPE: PRT
<213> ORGANISM: Artificial sequence
<220> FEATURE:
<223> OTHER INFORMATION: Synthetic peptide

<400> SEQUENCE: 55

Glu Val His Ser Thr Asp Arg Tyr Arg Ser Ile Pro
1               5                   10

<210> SEQ ID NO 56
<211> LENGTH: 12
<212> TYPE: PRT
<213> ORGANISM: Artificial sequence
<220> FEATURE:
<223> OTHER INFORMATION: Synthetic peptide

<400> SEQUENCE: 56

Phe Gly Leu Gln Pro Thr Gly Asp Ile Ala Arg Arg
1               5                   10

<210> SEQ ID NO 57
```

```
<211> LENGTH: 12
<212> TYPE: PRT
<213> ORGANISM: Artificial sequence
<220> FEATURE:
<223> OTHER INFORMATION: Synthetic peptide

<400> SEQUENCE: 57

Phe Ser Met Asp Asp Pro Glu Arg Val Arg Ser Pro
1               5                   10

<210> SEQ ID NO 58
<211> LENGTH: 12
<212> TYPE: PRT
<213> ORGANISM: Artificial sequence
<220> FEATURE:
<223> OTHER INFORMATION: Synthetic peptide

<400> SEQUENCE: 58

Phe Ser Pro Leu His Thr Ser Thr Tyr Arg Pro Ser
1               5                   10

<210> SEQ ID NO 59
<211> LENGTH: 12
<212> TYPE: PRT
<213> ORGANISM: Artificial sequence
<220> FEATURE:
<223> OTHER INFORMATION: Synthetic peptide

<400> SEQUENCE: 59

Gly Asp Phe Asn Ser Gly His His Thr Thr Thr Arg
1               5                   10

<210> SEQ ID NO 60
<211> LENGTH: 12
<212> TYPE: PRT
<213> ORGANISM: Artificial sequence
<220> FEATURE:
<223> OTHER INFORMATION: Synthetic peptide

<400> SEQUENCE: 60

Gly Pro Ser Asn Asn Leu Pro Trp Ser Asn Thr Pro
1               5                   10

<210> SEQ ID NO 61
<211> LENGTH: 12
<212> TYPE: PRT
<213> ORGANISM: Artificial sequence
<220> FEATURE:
<223> OTHER INFORMATION: Synthetic peptide

<400> SEQUENCE: 61

Gly Val His Lys His Phe Tyr Ser Arg Trp Leu Gly
1               5                   10

<210> SEQ ID NO 62
<211> LENGTH: 12
<212> TYPE: PRT
<213> ORGANISM: Artificial sequence
<220> FEATURE:
<223> OTHER INFORMATION: Synthetic peptide

<400> SEQUENCE: 62

His Ala Pro Leu Thr Arg Ser Pro Ala Pro Asn Leu
1               5                   10

<210> SEQ ID NO 63
<211> LENGTH: 12
```

```
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Phe or Leu

<400> SEQUENCE: 63

His Gly Ser Leu Thr Thr Leu Xaa Arg Tyr Glu Pro
 1               5                  10

<210> SEQ ID NO 64
<211> LENGTH: 12
<212> TYPE: PRT
<213> ORGANISM: Artificial sequence
<220> FEATURE:
<223> OTHER INFORMATION: Synthetic peptide

<400> SEQUENCE: 64

His His Phe His Leu Pro Lys Leu Arg Pro Pro Val
 1               5                  10

<210> SEQ ID NO 65
<211> LENGTH: 12
<212> TYPE: PRT
<213> ORGANISM: Artificial sequence
<220> FEATURE:
<223> OTHER INFORMATION: Synthetic peptide

<400> SEQUENCE: 65

His His Thr Trp Asp Thr Arg Ile Trp Gln Ala Phe
 1               5                  10

<210> SEQ ID NO 66
<211> LENGTH: 11
<212> TYPE: PRT
<213> ORGANISM: Artificial sequence
<220> FEATURE:
<223> OTHER INFORMATION: Synthetic peptide

<400> SEQUENCE: 66

His Pro Thr Thr Pro Ile His Met Pro Asn Phe
 1               5                  10

<210> SEQ ID NO 67
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Any amino acid
<220> FEATURE:
<221> NAME/KEY: misc_feature
<222> LOCATION: (7)..(7)
<223> OTHER INFORMATION: Pro or no amino acid
<220> FEATURE:
<221> NAME/KEY: misc_feature
<222> LOCATION: (11)..(11)
<223> OTHER INFORMATION: Ala or Gly

<400> SEQUENCE: 67

His Arg Asp Pro Xaa Ser Xaa Pro Ser Ala Xaa Arg Pro
 1               5                  10
```

```
<210> SEQ ID NO 68
<211> LENGTH: 12
<212> TYPE: PRT
<213> ORGANISM: Artificial sequence
<220> FEATURE:
<223> OTHER INFORMATION: Synthetic peptide

<400> SEQUENCE: 68

His Asn Val Thr Thr Arg Thr Gln Arg Leu Met Pro
1               5                   10

<210> SEQ ID NO 69
<211> LENGTH: 12
<212> TYPE: PRT
<213> ORGANISM: Artificial sequence
<220> FEATURE:
<223> OTHER INFORMATION: Synthetic peptide

<400> SEQUENCE: 69

His Ser Ala Cys His Ala Ser Leu Lys His Arg Cys
1               5                   10

<210> SEQ ID NO 70
<211> LENGTH: 12
<212> TYPE: PRT
<213> ORGANISM: Artificial sequence
<220> FEATURE:
<223> OTHER INFORMATION: Synthetic peptide

<400> SEQUENCE: 70

His Ser Ala Cys Lys Leu Thr Thr Cys Lys Asp Gly
1               5                   10

<210> SEQ ID NO 71
<211> LENGTH: 12
<212> TYPE: PRT
<213> ORGANISM: Artificial sequence
<220> FEATURE:
<223> OTHER INFORMATION: Synthetic peptide

<400> SEQUENCE: 71

His Ser Ala Cys Leu Ser Thr Lys Thr Asn Ile Cys
1               5                   10

<210> SEQ ID NO 72
<211> LENGTH: 12
<212> TYPE: PRT
<213> ORGANISM: Artificial sequence
<220> FEATURE:
<223> OTHER INFORMATION: Synthetic peptide

<400> SEQUENCE: 72

Ile Ala His Val Pro Glu Thr Arg Leu Ala Gln Met
1               5                   10

<210> SEQ ID NO 73
<211> LENGTH: 12
<212> TYPE: PRT
<213> ORGANISM: Artificial sequence
<220> FEATURE:
<223> OTHER INFORMATION: Synthetic peptide

<400> SEQUENCE: 73

Ile Phe Ser Met Gly Thr Ala Leu Ala Arg Pro Leu
1               5                   10

<210> SEQ ID NO 74
```

<211> LENGTH: 12
<212> TYPE: PRT
<213> ORGANISM: Artificial sequence
<220> FEATURE:
<223> OTHER INFORMATION: Synthetic peptide

<400> SEQUENCE: 74

Ile Asn Lys His Pro Gln Gln Val Ser Thr Leu Leu
1               5                   10

<210> SEQ ID NO 75
<211> LENGTH: 12
<212> TYPE: PRT
<213> ORGANISM: Artificial sequence
<220> FEATURE:
<223> OTHER INFORMATION: Synthetic peptide

<400> SEQUENCE: 75

Ile Ser Pro Ser His Ser Gln Ala Gln Ala Asp Leu
1               5                   10

<210> SEQ ID NO 76
<211> LENGTH: 12
<212> TYPE: PRT
<213> ORGANISM: Artificial sequence
<220> FEATURE:
<223> OTHER INFORMATION: Synthetic peptide

<400> SEQUENCE: 76

Leu Asp Tyr Pro Ile Pro Gln Thr Val Leu His His
1               5                   10

<210> SEQ ID NO 77
<211> LENGTH: 12
<212> TYPE: PRT
<213> ORGANISM: Artificial sequence
<220> FEATURE:
<223> OTHER INFORMATION: Synthetic peptide

<400> SEQUENCE: 77

Leu Phe Ala Ala Val Pro Ser Thr Gln Phe Phe Arg
1               5                   10

<210> SEQ ID NO 78
<211> LENGTH: 12
<212> TYPE: PRT
<213> ORGANISM: Artificial sequence
<220> FEATURE:
<223> OTHER INFORMATION: Synthetic peptide

<400> SEQUENCE: 78

Leu Gly Phe Asp Pro Thr Ser Thr Arg Phe Tyr Thr
1               5                   10

<210> SEQ ID NO 79
<211> LENGTH: 12
<212> TYPE: PRT
<213> ORGANISM: Artificial sequence
<220> FEATURE:
<223> OTHER INFORMATION: Synthetic peptide

<400> SEQUENCE: 79

Leu Leu Ala Asp Thr Thr His His Arg Pro Trp Pro
1               5                   10

<210> SEQ ID NO 80
<211> LENGTH: 12

<212> TYPE: PRT
<213> ORGANISM: Artificial sequence
<220> FEATURE:
<223> OTHER INFORMATION: Synthetic peptide

<400> SEQUENCE: 80

Leu Pro Trp Ala Pro Asn Leu Pro Asp Ser Thr Ala
1               5                   10

<210> SEQ ID NO 81
<211> LENGTH: 12
<212> TYPE: PRT
<213> ORGANISM: Artificial sequence
<220> FEATURE:
<223> OTHER INFORMATION: Synthetic peptide

<400> SEQUENCE: 81

Leu Gln Pro Ser Gln Pro Gln Arg Phe Ala Pro Thr
1               5                   10

<210> SEQ ID NO 82
<211> LENGTH: 12
<212> TYPE: PRT
<213> ORGANISM: Artificial sequence
<220> FEATURE:
<223> OTHER INFORMATION: Synthetic peptide

<400> SEQUENCE: 82

Leu Ser Pro Pro Met Gln Leu Gln Pro Thr Tyr Ser
1               5                   10

<210> SEQ ID NO 83
<211> LENGTH: 12
<212> TYPE: PRT
<213> ORGANISM: Artificial sequence
<220> FEATURE:
<223> OTHER INFORMATION: Synthetic peptide

<400> SEQUENCE: 83

Met His Asn Val Ser Asp Ser Asn Asp Ser Ala Ile
1               5                   10

<210> SEQ ID NO 84
<211> LENGTH: 12
<212> TYPE: PRT
<213> ORGANISM: Artificial sequence
<220> FEATURE:
<223> OTHER INFORMATION: Synthetic peptide

<400> SEQUENCE: 84

Asn Ser Ser Met Leu Gly Met Leu Pro Ser Ser Phe
1               5                   10

<210> SEQ ID NO 85
<211> LENGTH: 12
<212> TYPE: PRT
<213> ORGANISM: Artificial sequence
<220> FEATURE:
<223> OTHER INFORMATION: Synthetic peptide

<400> SEQUENCE: 85

Asn Thr Ser Ser Ser Gln Gly Thr Gln Arg Leu Gly
1               5                   10

<210> SEQ ID NO 86
<211> LENGTH: 12
<212> TYPE: PRT

<213> ORGANISM: Artificial sequence
<220> FEATURE:
<223> OTHER INFORMATION: Synthetic peptide

<400> SEQUENCE: 86

Pro Gly Gln Trp Pro Ser Ser Leu Thr Leu Tyr Lys
1               5                   10

<210> SEQ ID NO 87
<211> LENGTH: 12
<212> TYPE: PRT
<213> ORGANISM: Artificial sequence
<220> FEATURE:
<223> OTHER INFORMATION: Synthetic peptide

<400> SEQUENCE: 87

Gln Ile Pro Gln Met Arg Ile Leu His Pro Tyr Gly
1               5                   10

<210> SEQ ID NO 88
<211> LENGTH: 12
<212> TYPE: PRT
<213> ORGANISM: Artificial sequence
<220> FEATURE:
<223> OTHER INFORMATION: Synthetic peptide

<400> SEQUENCE: 88

Gln Ile Gln Lys Pro Pro Arg Thr Pro Pro Ser Leu
1               5                   10

<210> SEQ ID NO 89
<211> LENGTH: 12
<212> TYPE: PRT
<213> ORGANISM: Artificial sequence
<220> FEATURE:
<223> OTHER INFORMATION: Synthetic peptide

<400> SEQUENCE: 89

Gln Leu Thr Gln Thr Met Trp Lys Asp Thr Thr Leu
1               5                   10

<210> SEQ ID NO 90
<211> LENGTH: 12
<212> TYPE: PRT
<213> ORGANISM: Artificial sequence
<220> FEATURE:
<223> OTHER INFORMATION: Synthetic peptide

<400> SEQUENCE: 90

Gln Asn Leu Pro Pro Glu Arg Tyr Ser Glu Ala Thr
1               5                   10

<210> SEQ ID NO 91
<211> LENGTH: 12
<212> TYPE: PRT
<213> ORGANISM: Artificial sequence
<220> FEATURE:
<223> OTHER INFORMATION: Synthetic peptide

<400> SEQUENCE: 91

Gln Ser Leu Ser Phe Ala Gly Pro Pro Ala Trp Gln
1               5                   10

<210> SEQ ID NO 92
<211> LENGTH: 12
<212> TYPE: PRT
<213> ORGANISM: Artificial sequence

```
<220> FEATURE:
<223> OTHER INFORMATION: Synthetic peptide

<400> SEQUENCE: 92

Gln Thr Thr Met Thr Pro Leu Trp Pro Ser Phe Ser
1               5                   10

<210> SEQ ID NO 93
<211> LENGTH: 12
<212> TYPE: PRT
<213> ORGANISM: Artificial sequence
<220> FEATURE:
<223> OTHER INFORMATION: Synthetic peptide

<400> SEQUENCE: 93

Arg Cys Met Ser Glu Val Ile Ser Phe Asn Cys Pro
1               5                   10

<210> SEQ ID NO 94
<211> LENGTH: 12
<212> TYPE: PRT
<213> ORGANISM: Artificial sequence
<220> FEATURE:
<223> OTHER INFORMATION: Synthetic peptide

<400> SEQUENCE: 94

Arg Ser Pro Tyr Tyr Asn Lys Trp Ser Ser Lys Phe
1               5                   10

<210> SEQ ID NO 95
<211> LENGTH: 12
<212> TYPE: PRT
<213> ORGANISM: Artificial sequence
<220> FEATURE:
<223> OTHER INFORMATION: Synthetic peptide

<400> SEQUENCE: 95

Ser Ala Gly His Ile His Glu Ala His Arg Pro Leu
1               5                   10

<210> SEQ ID NO 96
<211> LENGTH: 12
<212> TYPE: PRT
<213> ORGANISM: Artificial sequence
<220> FEATURE:
<223> OTHER INFORMATION: Synthetic peptide

<400> SEQUENCE: 96

Ser Ala Ile Ser Asp His Arg Ala His Arg Ser His
1               5                   10

<210> SEQ ID NO 97
<211> LENGTH: 12
<212> TYPE: PRT
<213> ORGANISM: Artificial sequence
<220> FEATURE:
<223> OTHER INFORMATION: Synthetic peptide

<400> SEQUENCE: 97

Ser Glu Pro Thr Tyr Trp Arg Pro Asn Met Ser Gly
1               5                   10

<210> SEQ ID NO 98
<211> LENGTH: 12
<212> TYPE: PRT
<213> ORGANISM: Artificial sequence
<220> FEATURE:
```

```
<223> OTHER INFORMATION: Synthetic peptide

<400> SEQUENCE: 98

Ser Phe Ala Pro Asp Ile Lys Tyr Pro Val Pro Ser
1               5                   10

<210> SEQ ID NO 99
<211> LENGTH: 12
<212> TYPE: PRT
<213> ORGANISM: Artificial sequence
<220> FEATURE:
<223> OTHER INFORMATION: Synthetic peptide

<400> SEQUENCE: 99

Ser Phe Trp His His Ser Pro Arg Ser Pro Leu
1               5                   10

<210> SEQ ID NO 100
<211> LENGTH: 12
<212> TYPE: PRT
<213> ORGANISM: Artificial sequence
<220> FEATURE:
<223> OTHER INFORMATION: Synthetic peptide

<400> SEQUENCE: 100

Ser Ile Phe Ala His Gln Thr Pro Thr His Lys Asn
1               5                   10

<210> SEQ ID NO 101
<211> LENGTH: 12
<212> TYPE: PRT
<213> ORGANISM: Artificial sequence
<220> FEATURE:
<223> OTHER INFORMATION: Synthetic peptide

<400> SEQUENCE: 101

Ser Ile Pro Ser His Ser Ile His Ser Ala Lys Ala
1               5                   10

<210> SEQ ID NO 102
<211> LENGTH: 12
<212> TYPE: PRT
<213> ORGANISM: Artificial sequence
<220> FEATURE:
<223> OTHER INFORMATION: Synthetic peptide

<400> SEQUENCE: 102

Ser Ile Arg Thr Ser Met Asn Pro Pro Asn Leu Leu
1               5                   10

<210> SEQ ID NO 103
<211> LENGTH: 12
<212> TYPE: PRT
<213> ORGANISM: Artificial sequence
<220> FEATURE:
<223> OTHER INFORMATION: Synthetic peptide

<400> SEQUENCE: 103

Ser Leu Pro His Tyr Ile Asp Asn Pro Phe Arg Gln
1               5                   10

<210> SEQ ID NO 104
<211> LENGTH: 12
<212> TYPE: PRT
<213> ORGANISM: Artificial sequence
<220> FEATURE:
<223> OTHER INFORMATION: Synthetic peptide
```

```
<400> SEQUENCE: 104

Ser Leu Ser Lys Ala Asn Ile Leu His Leu Tyr Gly
1               5                   10

<210> SEQ ID NO 105
<211> LENGTH: 12
<212> TYPE: PRT
<213> ORGANISM: Artificial sequence
<220> FEATURE:
<223> OTHER INFORMATION: Synthetic peptide

<400> SEQUENCE: 105

Ser Leu Val Thr Ala Asp Ala Ser Phe Thr Pro Ser
1               5                   10

<210> SEQ ID NO 106
<211> LENGTH: 12
<212> TYPE: PRT
<213> ORGANISM: Artificial sequence
<220> FEATURE:
<223> OTHER INFORMATION: Synthetic peptide

<400> SEQUENCE: 106

Ser Met Val Tyr Gly Asn Arg Leu Pro Ser Ala Leu
1               5                   10

<210> SEQ ID NO 107
<211> LENGTH: 12
<212> TYPE: PRT
<213> ORGANISM: Artificial sequence
<220> FEATURE:
<223> OTHER INFORMATION: Synthetic peptide

<400> SEQUENCE: 107

Ser Pro Ser Leu Met Ala Arg Ser Ser Pro Tyr Trp
1               5                   10

<210> SEQ ID NO 108
<211> LENGTH: 12
<212> TYPE: PRT
<213> ORGANISM: Artificial sequence
<220> FEATURE:
<223> OTHER INFORMATION: Synthetic peptide

<400> SEQUENCE: 108

Ser Pro Asn Leu Pro Trp Ser Lys Leu Ser Ala Tyr
1               5                   10

<210> SEQ ID NO 109
<211> LENGTH: 12
<212> TYPE: PRT
<213> ORGANISM: Artificial sequence
<220> FEATURE:
<223> OTHER INFORMATION: Synthetic peptide

<400> SEQUENCE: 109

Ser Gln Thr Leu Pro Tyr Ser Asn Ala Pro Ser Pro
1               5                   10

<210> SEQ ID NO 110
<211> LENGTH: 12
<212> TYPE: PRT
<213> ORGANISM: Artificial sequence
<220> FEATURE:
<223> OTHER INFORMATION: Synthetic peptide
```

```
<400> SEQUENCE: 110

Ser Ser Thr Gln Ala His Pro Phe Ala Pro Gln Leu
1               5                   10

<210> SEQ ID NO 111
<211> LENGTH: 12
<212> TYPE: PRT
<213> ORGANISM: Artificial sequence
<220> FEATURE:
<223> OTHER INFORMATION: Synthetic peptide

<400> SEQUENCE: 111

Ser Thr Pro Asn Ser Tyr Ser Leu Pro Gln Ala Arg
1               5                   10

<210> SEQ ID NO 112
<211> LENGTH: 12
<212> TYPE: PRT
<213> ORGANISM: Artificial sequence
<220> FEATURE:
<223> OTHER INFORMATION: Synthetic peptide

<400> SEQUENCE: 112

Ser Thr Val Val Met Gln Pro Pro Arg Pro Ala
1               5                   10

<210> SEQ ID NO 113
<211> LENGTH: 12
<212> TYPE: PRT
<213> ORGANISM: Artificial sequence
<220> FEATURE:
<223> OTHER INFORMATION: Synthetic peptide

<400> SEQUENCE: 113

Ser Val Gln Thr Arg Pro Leu Phe His Ser His Phe
1               5                   10

<210> SEQ ID NO 114
<211> LENGTH: 12
<212> TYPE: PRT
<213> ORGANISM: Artificial sequence
<220> FEATURE:
<223> OTHER INFORMATION: Synthetic peptide

<400> SEQUENCE: 114

Ser Val Ser Val Gly Met Lys Pro Ser Pro Arg Pro
1               5                   10

<210> SEQ ID NO 115
<211> LENGTH: 12
<212> TYPE: PRT
<213> ORGANISM: Artificial sequence
<220> FEATURE:
<223> OTHER INFORMATION: Synthetic peptide

<400> SEQUENCE: 115

Ser Tyr Ile Asp Ser Met Val Pro Ser Thr Gln Thr
1               5                   10

<210> SEQ ID NO 116
<211> LENGTH: 12
<212> TYPE: PRT
<213> ORGANISM: Artificial sequence
<220> FEATURE:
<223> OTHER INFORMATION: Synthetic peptide

<400> SEQUENCE: 116
```

```
Ser Tyr Lys Thr Thr Asp Ser Asp Thr Ser Pro Leu
1               5                   10

<210> SEQ ID NO 117
<211> LENGTH: 12
<212> TYPE: PRT
<213> ORGANISM: Artificial sequence
<220> FEATURE:
<223> OTHER INFORMATION: Synthetic peptide

<400> SEQUENCE: 117

Thr Ala Ala Ala Ser Asn Leu Arg Ala Val Pro Pro
1               5                   10

<210> SEQ ID NO 118
<211> LENGTH: 12
<212> TYPE: PRT
<213> ORGANISM: Artificial sequence
<220> FEATURE:
<223> OTHER INFORMATION: Synthetic peptide

<400> SEQUENCE: 118

Thr Ala Pro Leu Ser His Pro Pro Arg Pro Gly Ala
1               5                   10

<210> SEQ ID NO 119
<211> LENGTH: 12
<212> TYPE: PRT
<213> ORGANISM: Artificial sequence
<220> FEATURE:
<223> OTHER INFORMATION: Synthetic peptide

<400> SEQUENCE: 119

Thr Gly Leu Leu Pro Asn Ser Ser Gly Ala Gly Ile
1               5                   10

<210> SEQ ID NO 120
<211> LENGTH: 12
<212> TYPE: PRT
<213> ORGANISM: Artificial sequence
<220> FEATURE:
<223> OTHER INFORMATION: Synthetic peptide

<400> SEQUENCE: 120

Thr Gly Pro Pro Ser Arg Gln Pro Ala Pro Leu His
1               5                   10

<210> SEQ ID NO 121
<211> LENGTH: 12
<212> TYPE: PRT
<213> ORGANISM: Artificial sequence
<220> FEATURE:
<223> OTHER INFORMATION: Synthetic peptide

<400> SEQUENCE: 121

Thr Leu Ser Asn Gly His Arg Tyr Leu Glu Leu Leu
1               5                   10

<210> SEQ ID NO 122
<211> LENGTH: 12
<212> TYPE: PRT
<213> ORGANISM: Artificial sequence
<220> FEATURE:
<223> OTHER INFORMATION: Synthetic peptide

<400> SEQUENCE: 122
```

Thr Pro Ser Pro Lys Leu Leu Gln Val Phe Gln Ala
1               5                   10

<210> SEQ ID NO 123
<211> LENGTH: 12
<212> TYPE: PRT
<213> ORGANISM: Artificial sequence
<220> FEATURE:
<223> OTHER INFORMATION: Synthetic peptide

<400> SEQUENCE: 123

Thr Pro Ser Thr Gly Leu Gly Met Ser Pro Ala Val
1               5                   10

<210> SEQ ID NO 124
<211> LENGTH: 12
<212> TYPE: PRT
<213> ORGANISM: Artificial sequence
<220> FEATURE:
<223> OTHER INFORMATION: Synthetic peptide

<400> SEQUENCE: 124

Thr Pro Val Tyr Ser Leu Lys Leu Gly Pro Trp Pro
1               5                   10

<210> SEQ ID NO 125
<211> LENGTH: 12
<212> TYPE: PRT
<213> ORGANISM: Artificial sequence
<220> FEATURE:
<223> OTHER INFORMATION: Synthetic peptide

<400> SEQUENCE: 125

Thr Arg Leu Val Pro Ser Arg Tyr Tyr His His Pro
1               5                   10

<210> SEQ ID NO 126
<211> LENGTH: 12
<212> TYPE: PRT
<213> ORGANISM: Artificial sequence
<220> FEATURE:
<223> OTHER INFORMATION: Synthetic peptide

<400> SEQUENCE: 126

Thr Ser Pro Ile Pro Gln Met Arg Thr Val Pro Pro
1               5                   10

<210> SEQ ID NO 127
<211> LENGTH: 12
<212> TYPE: PRT
<213> ORGANISM: Artificial sequence
<220> FEATURE:
<223> OTHER INFORMATION: Synthetic peptide

<400> SEQUENCE: 127

Thr Thr Asn Ser Ser Met Thr Met Gln Leu Gln Arg
1               5                   10

<210> SEQ ID NO 128
<211> LENGTH: 12
<212> TYPE: PRT
<213> ORGANISM: Artificial sequence
<220> FEATURE:
<223> OTHER INFORMATION: Synthetic peptide

<400> SEQUENCE: 128

Thr Thr Thr Leu Pro Val Gln Pro Thr Leu Arg Asn

```
1               5                   10
```

<210> SEQ ID NO 129
<211> LENGTH: 12
<212> TYPE: PRT
<213> ORGANISM: Artificial sequence
<220> FEATURE:
<223> OTHER INFORMATION: Synthetic peptide

<400> SEQUENCE: 129

```
Thr Thr Thr Trp Thr Thr Thr Ala Arg Trp Pro Leu
1               5                   10
```

<210> SEQ ID NO 130
<211> LENGTH: 12
<212> TYPE: PRT
<213> ORGANISM: Artificial sequence
<220> FEATURE:
<223> OTHER INFORMATION: Synthetic peptide

<400> SEQUENCE: 130

```
Thr Val Ala Gln Met Pro Pro His Trp Gln Leu Thr
1               5                   10
```

<210> SEQ ID NO 131
<211> LENGTH: 12
<212> TYPE: PRT
<213> ORGANISM: Artificial sequence
<220> FEATURE:
<223> OTHER INFORMATION: Synthetic peptide

<400> SEQUENCE: 131

```
Thr Trp Asn Ser Asn Ser Thr Gln Tyr Gly Asn Arg
1               5                   10
```

<210> SEQ ID NO 132
<211> LENGTH: 12
<212> TYPE: PRT
<213> ORGANISM: Artificial sequence
<220> FEATURE:
<223> OTHER INFORMATION: Synthetic peptide

<400> SEQUENCE: 132

```
Thr Trp Thr Leu Pro Ala Met His Pro Arg Pro Ala
1               5                   10
```

<210> SEQ ID NO 133
<211> LENGTH: 12
<212> TYPE: PRT
<213> ORGANISM: Artificial sequence
<220> FEATURE:
<223> OTHER INFORMATION: Synthetic peptide

<400> SEQUENCE: 133

```
Val His Thr Ser Leu Leu Gln Lys His Pro Leu Pro
1               5                   10
```

<210> SEQ ID NO 134
<211> LENGTH: 11
<212> TYPE: PRT
<213> ORGANISM: Artificial sequence
<220> FEATURE:
<223> OTHER INFORMATION: Synthetic peptide

<400> SEQUENCE: 134

```
Val Leu Pro Asn Ile Tyr Met Thr Leu Ser Ala
1               5                   10
```

```
<210> SEQ ID NO 135
<211> LENGTH: 12
<212> TYPE: PRT
<213> ORGANISM: Artificial sequence
<220> FEATURE:
<223> OTHER INFORMATION: Synthetic peptide

<400> SEQUENCE: 135

Val Met Asp Phe Ala Ser Pro Ala His Val Leu Pro
1               5                   10

<210> SEQ ID NO 136
<211> LENGTH: 12
<212> TYPE: PRT
<213> ORGANISM: Artificial sequence
<220> FEATURE:
<223> OTHER INFORMATION: Synthetic peptide

<400> SEQUENCE: 136

Val Asn Gln Glu Tyr Trp Phe Phe Pro Arg Arg Pro
1               5                   10

<210> SEQ ID NO 137
<211> LENGTH: 11
<212> TYPE: PRT
<213> ORGANISM: Artificial sequence
<220> FEATURE:
<223> OTHER INFORMATION: Synthetic peptide

<400> SEQUENCE: 137

Val Tyr Ser Ser Pro Leu Ser Gln Leu Pro Arg
1               5                   10

<210> SEQ ID NO 138
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Arg or no amino acid
<220> FEATURE:
<221> NAME/KEY: misc_feature
<222> LOCATION: (11)..(11)
<223> OTHER INFORMATION: Leu or no amino acid
<220> FEATURE:
<221> NAME/KEY: misc_feature
<222> LOCATION: (14)..(14)
<223> OTHER INFORMATION: Lys or no amino acid

<400> SEQUENCE: 138

Val Pro Pro Ile Ser Xaa Thr Phe Leu Phe Xaa Ser Thr Xaa Ser
1               5                   10                  15

<210> SEQ ID NO 139
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (11)..(11)
<223> OTHER INFORMATION: Any amino acid

<400> SEQUENCE: 139
```

Val Pro Pro Leu His Pro Ala Leu Ser Arg Xaa Asn
1               5                   10

<210> SEQ ID NO 140
<211> LENGTH: 12
<212> TYPE: PRT
<213> ORGANISM: Artificial sequence
<220> FEATURE:
<223> OTHER INFORMATION: Synthetic peptide

<400> SEQUENCE: 140

Val Ser Pro Phe Leu Ser Pro Thr Pro Leu Leu Phe
1               5                   10

<210> SEQ ID NO 141
<211> LENGTH: 12
<212> TYPE: PRT
<213> ORGANISM: Artificial sequence
<220> FEATURE:
<223> OTHER INFORMATION: Synthetic peptide

<400> SEQUENCE: 141

Val Ser Arg Leu Gly Thr Pro Ser Met His Pro Ser
1               5                   10

<210> SEQ ID NO 142
<211> LENGTH: 12
<212> TYPE: PRT
<213> ORGANISM: Artificial sequence
<220> FEATURE:
<223> OTHER INFORMATION: Synthetic peptide

<400> SEQUENCE: 142

Trp Pro Phe Asn His Phe Pro Trp Trp Asn Val Pro
1               5                   10

<210> SEQ ID NO 143
<211> LENGTH: 12
<212> TYPE: PRT
<213> ORGANISM: Artificial sequence
<220> FEATURE:
<223> OTHER INFORMATION: Synthetic peptide

<400> SEQUENCE: 143

Trp Ser Ala His Ile Val Pro Tyr Ser His Lys Pro
1               5                   10

<210> SEQ ID NO 144
<211> LENGTH: 12
<212> TYPE: PRT
<213> ORGANISM: Artificial sequence
<220> FEATURE:
<223> OTHER INFORMATION: Synthetic peptide

<400> SEQUENCE: 144

Trp Trp Pro Asn Ser Leu Asn Trp Val Pro Arg Pro
1               5                   10

<210> SEQ ID NO 145
<211> LENGTH: 12
<212> TYPE: PRT
<213> ORGANISM: Artificial sequence
<220> FEATURE:
<223> OTHER INFORMATION: Synthetic peptide

<400> SEQUENCE: 145

Tyr Ala Thr Gln His Asn Trp Arg Leu Lys His Glu

```
1               5                   10
```

<210> SEQ ID NO 146
<211> LENGTH: 10
<212> TYPE: PRT
<213> ORGANISM: Artificial sequence
<220> FEATURE:
<223> OTHER INFORMATION: Synthetic peptide

<400> SEQUENCE: 146

```
Tyr Cys Pro Met Arg Leu Cys Thr Asp Cys
1               5                   10
```

<210> SEQ ID NO 147
<211> LENGTH: 12
<212> TYPE: PRT
<213> ORGANISM: Artificial sequence
<220> FEATURE:
<223> OTHER INFORMATION: Synthetic peptide

<400> SEQUENCE: 147

```
Tyr Gly Lys Gly Phe Ser Pro Tyr Phe His Val Thr
1               5                   10
```

<210> SEQ ID NO 148
<211> LENGTH: 12
<212> TYPE: PRT
<213> ORGANISM: Artificial sequence
<220> FEATURE:
<223> OTHER INFORMATION: Synthetic peptide

<400> SEQUENCE: 148

```
Tyr Pro His Tyr Ser Leu Pro Gly Ser Ser Thr Leu
1               5                   10
```

<210> SEQ ID NO 149
<211> LENGTH: 12
<212> TYPE: PRT
<213> ORGANISM: Artificial sequence
<220> FEATURE:
<223> OTHER INFORMATION: Synthetic peptide

<400> SEQUENCE: 149

```
Tyr Pro Ser Leu Leu Lys Met Gln Pro Gln Phe Ser
1               5                   10
```

<210> SEQ ID NO 150
<211> LENGTH: 12
<212> TYPE: PRT
<213> ORGANISM: Artificial sequence
<220> FEATURE:
<223> OTHER INFORMATION: Synthetic peptide

<400> SEQUENCE: 150

```
Tyr Gln Pro Arg Pro Phe Val Thr Thr Ser Pro Met
1               5                   10
```

<210> SEQ ID NO 151
<211> LENGTH: 12
<212> TYPE: PRT
<213> ORGANISM: Artificial sequence
<220> FEATURE:
<223> OTHER INFORMATION: Synthetic peptide

<400> SEQUENCE: 151

```
Tyr Ser Ala Pro Leu Ala Arg Ser Asn Val Val Met
1               5                   10
```

<210> SEQ ID NO 152
<211> LENGTH: 12
<212> TYPE: PRT
<213> ORGANISM: Artificial sequence
<220> FEATURE:
<223> OTHER INFORMATION: Synthetic peptide

<400> SEQUENCE: 152

Tyr Thr Arg Leu Ser His Asn Pro Tyr Thr Leu Ser
1               5                   10

<210> SEQ ID NO 153
<211> LENGTH: 12
<212> TYPE: PRT
<213> ORGANISM: Artificial sequence
<220> FEATURE:
<223> OTHER INFORMATION: Synthetic peptide

<400> SEQUENCE: 153

Tyr Thr Thr His Val Leu Pro Phe Ala Pro Ser Ser
1               5                   10

<210> SEQ ID NO 154
<211> LENGTH: 12
<212> TYPE: PRT
<213> ORGANISM: Artificial sequence
<220> FEATURE:
<223> OTHER INFORMATION: Synthetic peptide

<400> SEQUENCE: 154

Tyr Thr Trp Gln Thr Ile Arg Glu Gln Tyr Glu Met
1               5                   10

<210> SEQ ID NO 155
<211> LENGTH: 9
<212> TYPE: PRT
<213> ORGANISM: Artificial sequence
<220> FEATURE:
<223> OTHER INFORMATION: Synthetic peptide

<400> SEQUENCE: 155

Cys Leu Ser Thr Lys Thr Asn Ile Cys
1               5

<210> SEQ ID NO 156
<211> LENGTH: 10
<212> TYPE: PRT
<213> ORGANISM: Artificial sequence
<220> FEATURE:
<223> OTHER INFORMATION: Synthetic peptide

<400> SEQUENCE: 156

Ala Cys Leu Ser Thr Lys Thr Asn Ile Cys
1               5                   10

<210> SEQ ID NO 157
<211> LENGTH: 9
<212> TYPE: PRT
<213> ORGANISM: Artificial sequence
<220> FEATURE:
<223> OTHER INFORMATION: Synthetic peptide

<400> SEQUENCE: 157

Cys Thr Thr Pro Ser Lys His Gln Cys
1               5

```
<210> SEQ ID NO 158
<211> LENGTH: 283
<212> TYPE: PRT
<213> ORGANISM: Artificial sequence
<220> FEATURE:
<223> OTHER INFORMATION: BKT-P2-FC polypeptide

<400> SEQUENCE: 158

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Ser Ile Pro Ser His Ser Ile His Ser Ala Lys Ala Gly Gly Gly Ser
        35                  40                  45

Lys Gly Phe Glu Pro Lys Ser Cys Asp Lys Thr His Thr Cys Pro Pro
    50                  55                  60

Cys Pro Ala Pro Glu Leu Leu Gly Gly Pro Ser Val Phe Leu Phe Pro
65                  70                  75                  80

Pro Lys Pro Lys Asp Thr Leu Met Ile Ser Arg Thr Pro Glu Val Thr
                85                  90                  95

Cys Val Val Val Asp Val Ser His Glu Asp Pro Glu Val Lys Phe Asn
            100                 105                 110

Trp Tyr Val Asp Gly Val Glu Val His Asn Ala Lys Thr Lys Pro Arg
        115                 120                 125

Glu Glu Gln Tyr Ala Ser Thr Tyr Arg Val Val Ser Val Leu Thr Val
    130                 135                 140

Leu His Gln Asp Trp Leu Asn Gly Lys Glu Tyr Lys Cys Lys Val Ser
145                 150                 155                 160

Asn Lys Ala Leu Pro Ala Pro Ile Glu Lys Thr Ile Ser Lys Ala Lys
                165                 170                 175

Gly Gln Pro Arg Glu Pro Gln Val Tyr Thr Leu Pro Pro Ser Arg Asp
            180                 185                 190

Glu Leu Thr Lys Asn Gln Val Ser Leu Thr Cys Leu Val Lys Gly Phe
        195                 200                 205

Tyr Pro Ser Asp Ile Ala Val Glu Trp Glu Ser Asn Gly Gln Pro Glu
    210                 215                 220

Asn Asn Tyr Lys Thr Thr Pro Pro Val Leu Asp Ser Asp Gly Ser Phe
225                 230                 235                 240

Phe Leu Tyr Ser Lys Leu Thr Val Asp Lys Ser Arg Trp Gln Gln Gly
                245                 250                 255

Asn Val Phe Ser Cys Ser Val Met His Glu Ala Leu His Asn His Tyr
            260                 265                 270

Thr Gln Lys Ser Leu Ser Leu Ser Pro Gly Lys
        275                 280

<210> SEQ ID NO 159
<211> LENGTH: 283
<212> TYPE: PRT
<213> ORGANISM: Artificial sequence
<220> FEATURE:
<223> OTHER INFORMATION: BKT-P46-FC polypeptide

<400> SEQUENCE: 159

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30
```

Leu Asp Tyr Pro Ile Pro Gln Thr Val Leu His His Gly Gly Ser
            35                  40                  45

Lys Gly Phe Glu Pro Lys Ser Cys Asp Lys Thr His Thr Cys Pro Pro
 50                  55                  60

Cys Pro Ala Pro Glu Leu Leu Gly Gly Pro Ser Val Phe Leu Phe Pro
 65                  70                  75                  80

Pro Lys Pro Lys Asp Thr Leu Met Ile Ser Arg Thr Pro Glu Val Thr
                 85                  90                  95

Cys Val Val Val Asp Val Ser His Glu Asp Pro Glu Val Lys Phe Asn
            100                 105                 110

Trp Tyr Val Asp Gly Val Glu Val His Asn Ala Lys Thr Lys Pro Arg
        115                 120                 125

Glu Glu Gln Tyr Ala Ser Thr Tyr Arg Val Val Ser Val Leu Thr Val
    130                 135                 140

Leu His Gln Asp Trp Leu Asn Gly Lys Glu Tyr Lys Cys Lys Val Ser
145                 150                 155                 160

Asn Lys Ala Leu Pro Ala Pro Ile Glu Lys Thr Ile Ser Lys Ala Lys
                165                 170                 175

Gly Gln Pro Arg Glu Pro Gln Val Tyr Thr Leu Pro Pro Ser Arg Asp
            180                 185                 190

Glu Leu Thr Lys Asn Gln Val Ser Leu Thr Cys Leu Val Lys Gly Phe
        195                 200                 205

Tyr Pro Ser Asp Ile Ala Val Glu Trp Glu Ser Asn Gly Gln Pro Glu
    210                 215                 220

Asn Asn Tyr Lys Thr Thr Pro Pro Val Leu Asp Ser Asp Gly Ser Phe
225                 230                 235                 240

Phe Leu Tyr Ser Lys Leu Thr Val Asp Lys Ser Arg Trp Gln Gln Gly
                245                 250                 255

Asn Val Phe Ser Cys Ser Val Met His Glu Ala Leu His Asn His Tyr
            260                 265                 270

Thr Gln Lys Ser Leu Ser Leu Ser Pro Gly Lys
        275                 280

<210> SEQ ID NO 160
<211> LENGTH: 233
<212> TYPE: PRT
<213> ORGANISM: Artificial sequence
<220> FEATURE:
<223> OTHER INFORMATION: Human IgG1 Fc (Fc N297A)

<400> SEQUENCE: 160

Phe Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Ala Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

```
Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 161
<211> LENGTH: 32
<212> TYPE: PRT
<213> ORGANISM: Artificial sequence
<220> FEATURE:
<223> OTHER INFORMATION: IL6 signal peptide

<400> SEQUENCE: 161

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

<210> SEQ ID NO 162
<211> LENGTH: 6
<212> TYPE: PRT
<213> ORGANISM: Artificial sequence
<220> FEATURE:
<223> OTHER INFORMATION: Hexapeptide spacer sequence

<400> SEQUENCE: 162

Gly Gly Gly Ser Lys Gly
1               5

<210> SEQ ID NO 163
<211> LENGTH: 36
<212> TYPE: DNA
<213> ORGANISM: Artificial sequence
<220> FEATURE:
<223> OTHER INFORMATION: BKT-P2 peptide DNA coding sequence

<400> SEQUENCE: 163
agcatcccca gccacagcat ccacagcgcc aaggcc                              36

<210> SEQ ID NO 164
<211> LENGTH: 36
<212> TYPE: DNA
<213> ORGANISM: Artificial sequence
<220> FEATURE:
<223> OTHER INFORMATION: BKT-P46 peptide DNA coding sequence

<400> SEQUENCE: 164
ctggactacc ctatccctca gaccgtgctg caccac                              36
```

-continued

```
<210> SEQ ID NO 165
<211> LENGTH: 702
<212> TYPE: DNA
<213> ORGANISM: Artificial sequence
<220> FEATURE:
<223> OTHER INFORMATION: Human IgG1 Fc (Fc N297A) DNA coding sequence

<400> SEQUENCE: 165 ttcgaacccca agagctgtga caagacccac acctgccccc cttgccctgc ccctgagctg      60
ctgggcggac ccagcgtgtt cctgttccct cccaagccta aggacaccct gatgatcagc     120 agaaccccccg aggtgacctg tgtggtggtg gatgtgagcc acgaggaccc tgaggtgaag     180
ttcaactggt acgtggacgg cgtggaggtg cacaatgcca agaccaagcc cagggaggag     240
cagtacgcca gcacctaccg ggtggtgtcc gtgctgaccg tgctgcacca ggattggctg     300
aacggcaagg aatacaagtg taaggtgtcc aacaaggccc tgcctgcccc tatcgagaaa     360
accatcagca aggccaaggg ccagcctagg gagccccagg tgtacaccct gccccctagc     420
agagatgagc tgaccaagaa tcaggtgtcc ctgacctgcc tggtgaaggg cttctacccc     480
agcgacatcg ccgtggagtg ggagagcaac ggccagcccg agaacaacta caagaccacc     540 cccctgtgc tggacagcga tggcagcttc ttcctgtaca gcaagctgac cgtggataag     600
agcagatggc agcagggcaa cgtgttcagc tgctccgtga tgcacgaggc cctgcacaat     660
cactacaccc agaagagcct gagcctgtcc cctggcaagt ga                        702

<210> SEQ ID NO 166
<211> LENGTH: 96
<212> TYPE: DNA
<213> ORGANISM: Artificial sequence
<220> FEATURE:
<223> OTHER INFORMATION: IL6 signal peptide DNA coding sequence

<400> SEQUENCE: 166
atgaacagct tcagcaccag cgccttcggc cccgtggcct tcagcctggg cctgctgctg      60
gtgctgcctg ccgccttccc tgccccgtg cccccc                                 96

<210> SEQ ID NO 167
<211> LENGTH: 18
<212> TYPE: DNA
<213> ORGANISM: Artificial sequence
<220> FEATURE:
<223> OTHER INFORMATION: Spacer DNA coding sequence

<400> SEQUENCE: 167
ggcggcggca gcaagggc                                                     18

<210> SEQ ID NO 168
<211> LENGTH: 852
<212> TYPE: DNA
<213> ORGANISM: Artificial sequence
<220> FEATURE:
<223> OTHER INFORMATION: IL6-P2-Fc N297A DNA coding sequence

<400> SEQUENCE: 168
atgaacagct tcagcaccag cgccttcggc cccgtggcct tcagcctggg cctgctgctg      60
gtgctgcctg ccgccttccc tgccccgtg cccccagca tccccagcca agcatccac       120 agcgccaagg ccggcggcgg cagcaagggc ttcgaaccca agagctgtga caagacccac     180
acctgccccc cttgccctgc ccctgagctg ctgggcggac ccagcgtgtt cctgttccct     240
cccaagccta aggacaccct gatgatcagc agaaccccccg aggtgacctg tgtggtggtg   300
```

```
gatgtgagcc acgaggaccc tgaggtgaag ttcaactggt acgtggacgg cgtggaggtg      360
cacaatgcca agaccaagcc cagggaggag cagtacgcca gcacctaccg ggtggtgtcc      420
gtgctgaccg tgctgcacca ggattggctg aacggcaagg aatacaagtg taaggtgtcc      480
aacaaggccc tgcctgcccc tatcgagaaa accatcagca aggccaaggg ccagcctagg      540
gagccccagg tgtacaccct gcccccctagc agagatgagc tgaccaagaa tcaggtgtcc      600
ctgacctgcc tggtgaaggg cttctacccc agcgacatcg ccgtggagtg ggagagcaac      660
ggccagcccg agaacaacta caagaccacc cccctgtgc tggacagcga tggcagcttc       720
ttcctgtaca gcaagctgac cgtggataag agcagatggc agcagggcaa cgtgttcagc      780
tgctccgtga tgcacgaggc cctgcacaat cactacaccc agaagagcct gagcctgtcc      840
cctggcaagt ga                                                          852
```

<210> SEQ ID NO 169
<211> LENGTH: 852
<212> TYPE: DNA
<213> ORGANISM: Artificial sequence
<220> FEATURE:
<223> OTHER INFORMATION: IL6-P46-Fc N297A DNA coding sequence

<400> SEQUENCE: 169

```
atgaacagct tcagcaccag cgccttcggc cccgtggcct tcagcctggg cctgctgctg       60
gtgctgcctg ccgccttccc tgccccccgtg ccccccctgg actaccctat ccctcagacc     120
gtgctgcacc acggcggcgg cagcaagggc ttcgaaccca gagctgtga caagacccac       180 acctgccccc cttgccctgc ccctgagctg ctgggcggac ccagcgtgtt cctgttccct      240
cccaagccta aggacaccct gatgatcagc agaacccccg aggtgacctg tgtggtggtg      300
gatgtgagcc acgaggaccc tgaggtgaag ttcaactggt acgtggacgg cgtggaggtg      360
cacaatgcca agaccaagcc cagggaggag cagtacgcca gcacctaccg ggtggtgtcc      420
gtgctgaccg tgctgcacca ggattggctg aacggcaagg aatacaagtg taaggtgtcc      480
aacaaggccc tgcctgcccc tatcgagaaa accatcagca aggccaaggg ccagcctagg      540
gagccccagg tgtacaccct gcccccctagc agagatgagc tgaccaagaa tcaggtgtcc    600
ctgacctgcc tggtgaaggg cttctacccc agcgacatcg ccgtggagtg ggagagcaac      660
ggccagcccg agaacaacta caagaccacc cccctgtgc tggacagcga tggcagcttc       720
ttcctgtaca gcaagctgac cgtggataag agcagatggc agcagggcaa cgtgttcagc      780
tgctccgtga tgcacgaggc cctgcacaat cactacaccc agaagagcct gagcctgtcc      840
cctggcaagt ga                                                          852
```

<210> SEQ ID NO 170
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 170

```
taatacgact cactataggg                                                   20
```

<210> SEQ ID NO 171
<211> LENGTH: 45
<212> TYPE: DNA
<213> ORGANISM: Artificial sequence
<220> FEATURE:
<223> OTHER INFORMATION: Single strand DNA oligonucleotide

```
<400> SEQUENCE: 171
ctgtggatgc tgtggctggg gatgctgggg ggcacggggg caggg                45

<210> SEQ ID NO 172
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 172
cacggtctga gggatagggt agtccagggg gggcacgggg gcagg                45

<210> SEQ ID NO 173
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 173
cgcttcgaag cccttgctgc cgccgccggc cttggcgctg tggatgctgt ggctgg     56

<210> SEQ ID NO 174
<211> LENGTH: 55
<212> TYPE: DNA
<213> ORGANISM: Artificial sequence
<220> FEATURE:
<223> OTHER INFORMATION: Single strand DNA oligonucleotide

<400> SEQUENCE: 174
cgcttcgaag cccttgctgc cgccgccgtg gtgcagcacg gtctgaggga taggg      55
```

CHEMOKINE BINDING POLYPEPTIDES FOR TREATING AUTOIMMUNITY AND INFLAMMATION

RELATED APPLICATIONS

This application is a division of U.S. patent application Ser. No. 13/378,063 filed on Dec. 14, 2011 now U.S. Pat. No. 8,085,398, which is a National Phase of PCT Patent Application No. PCT/IL2010/000473 having International filing date of Jun. 15, 2010, which claims the benefit of priority of U.S. Provisional Patent Application No. 61/213,493 filed on Jun. 15, 2009. The contents of the above applications are all incorporated herein by reference.

SEQUENCE LISTING STATEMENT

The ASCII file, entitled 58382SequenceListing.txt, created on Feb. 12, 2014, comprising 47,408 bytes, submitted concurrently with the filing of this application is incorporated herein by reference.

FIELD AND BACKGROUND OF THE INVENTION

The present invention discloses novel polypeptides which are capable of binding chemokines, and more particularly, but not exclusively, to polypeptides capable of modulating chemokine-dependent processes such as autoimmunity, inflammation, and cancer.

Chemokines are among the many biological factors that are involved in the inflammatory disease process. Chemokines belong to a group of small, ~8-14 kDa, mostly basic, heparin-binding proteins that are related both in their primary structure and the presence of 4 conserved cysteine residues.

The chemokines are chemotactic cytokines that have been shown to be selective chemoattractants for leukocyte subpopulations in vitro, and to elicit the accumulation of inflammatory cells in vivo. In addition to chemotaxis, chemokines mediate leukocyte de-granulation [Baggiolini and Dahinden, *Immunol Today* 1994, 15:127-133], up-regulation of adhesion receptors [Vaddi and Newton, *J Immunol* 1994, 153:4721-4732], and suppression of human immunodeficiency virus replication [Cocchi et al., *Science* 1995, 270:1811-1815].

Chemokines play an essential role in the recruitment and activation of cells from the immune system. They also have a wide range of effects in many different cell types beyond the immune system, including for example, in various cells of the central nervous system [Ma et al., *PNAS* 1998, 95:9448-9453], and in endothelial cells, where they result in either angiogenic or angiostatic effects [Strieter et al., *J Biol Chem* 1995, 270:27348-27357]. Particular chemokines may have multiple effects on tumors, including angiogenesis, promotion of growth and metastasis, and suppression of the immune response to cancer, while other chemokines inhibit tumor-mediated angiogenesis and promote anti-tumor immune responses.

Chemokine receptors have received increasing attention due to their critical role in the progression of inflammation and associated conditions such as asthma, atherosclerosis, graft rejection, AIDS and autoimmune conditions (e.g., multiple sclerosis, arthritis, myasthenia gravis, lupus).

International Patent Application PCT/IL03/00155 (published as WO 03/072599) and U.S. Pat. No. 7,488,717 disclose novel peptides and peptidomimetics, which are capable of binding chemokines and modulating their biological functions.

SUMMARY OF THE INVENTION

According to an aspect of some embodiments of the present invention there is provided an isolated polypeptide comprising at least one chemokine-binding peptide attached to an Fc domain or fragment thereof.

According to an aspect of some embodiments of the present invention there is provided a pharmaceutical composition comprising the polypeptide described herein and a pharmaceutically acceptable carrier.

According to an aspect of some embodiments of the present invention there is provided a use of the polypeptide described herein in the manufacture of a medicament for modulating a biological effect of a chemokine.

According to an aspect of some embodiments of the present invention there is provided a method of modulating a biological effect of a chemokine, the method comprising administering a therapeutically effective amount of the polypeptide described herein to a subject in need thereof, thereby modulating the biological effect of the chemokine.

According to an aspect of some embodiments of the present invention there is provided a use of the polypeptide described herein in the manufacture of a medicament for treating a condition selected from the group consisting of an inflammation, an allergy, delayed type hypersensitivity, a non-optimal immune response, abnormal cell migration, an autoimmune reaction, rheumatoid arthritis, systemic lupus erythematosis, multiple sclerosis, an allograft rejection, diabetes, sepsis, cancer, a malignant cell growth, a bacterial infection, a viral infection, arthritis, colitis, psoriasis, atherosclerosis, hypertension, myasthenia gravis and reperfusion ischemia.

According to an aspect of some embodiments of the present invention there is provided a method of treating a condition selected from the group consisting of an inflammation, an allergy, delayed type hypersensitivity, a non-optimal immune response, abnormal cell migration, an autoimmune reaction, rheumatoid arthritis, systemic lupus erythematosis, multiple sclerosis, an allograft rejection, diabetes, sepsis, cancer, a malignant cell growth, a bacterial infection, a viral infection, arthritis, colitis, psoriasis, atherosclerosis, hypertension, myasthenia gravis and reperfusion ischemia, the method comprising administering the polypeptide described herein to a subject in need thereof, thereby modulating and/or inhibiting the biological effect of the chemokine.

According to an aspect of some embodiments of the present invention there is provided an isolated polynucleotide encoding the polypeptide described herein.

According to an aspect of some embodiments of the present invention there is provided a nucleic acid construct comprising the polynucleotide described herein.

According to an aspect of some embodiments of the present invention there is provided a cell comprising the abovementioned nucleic acid construct.

According to an aspect of some embodiments of the present invention there is provided a method of generating a polypeptide, comprising culturing the abovementioned cell, and isolating the polypeptide.

According to an aspect of some embodiments of the present invention there is provided a conjugate comprising the polypeptide described herein attached to a water-soluble polymer.

According to some embodiments of the invention, the polypeptide further comprises a linker.

According to some embodiments of the invention, the linker is an amino acid linker.

According to some embodiments of the invention, the Fc domain is selected from the group consisting of an IgG Fc domain, an IgA Fc domain, an IgD Fc domain, an IgE Fc domain and an IgM Fc domain.

According to some embodiments of the invention, the chemokine-binding peptide is attached to an N terminus of the Fc domain or fragment thereof.

According to some embodiments of the invention, the chemokine-binding peptide is attached to a C terminus of the Fc domain or fragment thereof.

According to some embodiments of the invention, the linker is composed of 4 to 10 amino acids.

According to some embodiments of the invention, the linker is a hexapeptide.

According to some embodiments of the invention, the linker is a peptide set forth in SEQ ID NO: 162.

According to some embodiments of the invention, the polypeptide further comprises a signal peptide.

According to some embodiments of the invention, the signal peptide is at the N-terminus of the polypeptide.

According to some embodiments of the invention, the polypeptide has the formula:

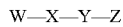

wherein:

W is a signal peptide;

X is the chemokine-binding peptide;

Y is the linker; and

Z is the Fc domain or fragment thereof.

According to some embodiments of the invention, the chemokine-binding peptide is from 10 to 20 amino acids in length.

According to some embodiments of the invention, the chemokine-binding peptide is from 12 to 13 amino acids in length.

According to some embodiments of the invention, the chemokine-binding peptide is characterized by an ability to bind to at least one chemokine selected from the group consisting of I-TAC, IP-10, MIG, MCP-1, eotaxin and RANTES.

According to some embodiments of the invention, the chemokine-binding peptide is selected from the group consisting of SEQ ID NOs: 1-157.

According to some embodiments of the invention, the chemokine-binding peptide is selected from the group consisting of BKT-P2 (SEQ ID NO: 101) and BKT-P46 (SEQ ID NO: 76).

According to some embodiments of the invention, the chemokine-binding peptide has an amino acid sequence showing at least 90% sequence homology to an amino acid sequence selected from the group consisting of SEQ ID NOs: 1-157.

According to some embodiments of the invention, the abovementioned sequence homology is at least 95%.

According to some embodiments of the invention, the signal peptide comprises an IL-6 signal peptide.

According to some embodiments of the invention, the signal peptide has SEQ ID NO: 161.

According to some embodiments of the invention, the signal peptide has an amino acid sequence showing at least 90% sequence homology to SEQ ID NO: 161.

According to some embodiments of the invention, the Fc domain is a human Fc domain.

According to some embodiments of the invention, the Fc domain is an IgG Fc domain.

According to some embodiments of the invention, the Fc domain is an IgG1 domain.

According to some embodiments of the invention, the Fc domain or fragment thereof is non-glycosylated.

According to some embodiments of the invention, the Fc domain or fragment thereof has SEQ ID NO: 160.

According to some embodiments of the invention, the polypeptide is characterized by an ability to inhibit binding of at least one chemokine to a chemokine receptor.

According to some embodiments of the invention, the polypeptide is characterized by an ability to enhance binding of at least one chemokine to a chemokine receptor.

According to some embodiments of the invention, the pharmaceutical composition is packaged in a packaging material and identified, in or on the packaging material, for use in modulating a biological effect of a chemokine.

According to some embodiments of the invention, the pharmaceutical composition is packaged in a packaging material and identified, in or on the packaging material, for use in treating a condition selected from the group consisting of an inflammation, an allergy, delayed type hypersensitivity, a non-optimal immune response, an autoimmune reaction, rheumatoid arthritis, systemic lupus erythematosis, multiple sclerosis, an allograft rejection, diabetes, sepsis, cancer, a malignant cell growth, a bacterial infection, a viral infection, arthritis, colitis, psoriasis, atherosclerosis, hypertension, myasthenia gravis and reperfusion ischemia.

According to some embodiments of the invention, the pharmaceutical composition is formulated for intravenous administration, oral administration, sub-cutaneous administration, topical administration and/or intranasal administration.

According to some embodiments of the invention, the medicament is formulated for intravenous administration, oral administration, sub-cutaneous administration, topical administration and/or intranasal administration.

According to some embodiments of the invention, administering comprises intravenous administration, oral administration, sub-cutaneous administration, topical administration and/or intranasal administration.

According to some embodiments of the invention, modulating comprises inhibiting.

According to some embodiments of the invention, the chemokine is selected from the group consisting of I-TAC, IP-10, MIG, MCP-1, eotaxin and RANTES.

According to some embodiments of the invention, the biological effect is selected from the group consisting of an inflammatory effect, cell migration, tumor growth, and cancer metastasis.

According to some embodiments of the invention, the polypeptide is for treating a condition selected from the group consisting of an inflammation, an allergy, delayed type hypersensitivity, a non-optimal immune response, abnormal cell migration, an autoimmune reaction, rheumatoid arthritis, systemic lupus erythematosis, multiple sclerosis, an allograft rejection, diabetes, sepsis, cancer, a malignant cell growth, a bacterial infection, a viral infection, arthritis, colitis, psoriasis, atherosclerosis, hypertension, myasthenia gravis and reperfusion ischemia.

According to some embodiments of the invention, the isolated polynucleotide has a nucleic acid sequence selected from the group consisting of SEQ ID NO: 168 and SEQ ID NO: 169.

According to some embodiments of the invention, the water-soluble polymer is polyethylene glycol.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A) and SEQ ID NO: 159 (BKT-P46-FC; FIG. 1B), and which further encode genes for resistance to ampicillin (Amp) and puromycin (Puro);

DESCRIPTION OF SPECIFIC EMBODIMENTS
OF THE INVENTION

The present invention discloses novel polypeptides which are capable of binding chemokines, and more particularly, but not exclusively, to polypeptides capable of modulating chemokine-dependent processes such as autoimmunity, inflammation, and cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As mentioned in the Background section hereinabove, peptides and structurally related compounds (peptidomimetics) have been described (e.g., in International Patent Application PCT/IL03/00155 (published as WO 03/072599) and U.S. Pat. No. 7,488,717), which are capable of binding to chemokines and modulating their biological functions. Examples of such peptides are set forth in SEQ ID NOs: 1-157. Due to their ability to modulate chemokine functions, such peptides have a variety of therapeutic applications. However, the therapeutic benefits of such peptides are typically limited, for example, by the short half-life of peptides in vivo.

While seeking to generate chemokine-binding peptides with improved properties, the present inventors attached a chemokine-binding peptide to an Fc domain fragment.

As is demonstrated in the Examples section that follows, while reducing the present invention to practice, it was found that polypeptides comprising a chemokine-binding peptide and an Fc domain fragment surprisingly exhibit improved chemokine-binding capabilities. It was further found that the polypeptides exhibit improved efficacy in vivo for treating immune-related diseases and disorders, such as multiple sclerosis, arthritis and delayed type hypersensitivity, as well as a long circulation lifetime.

Figure 1A:
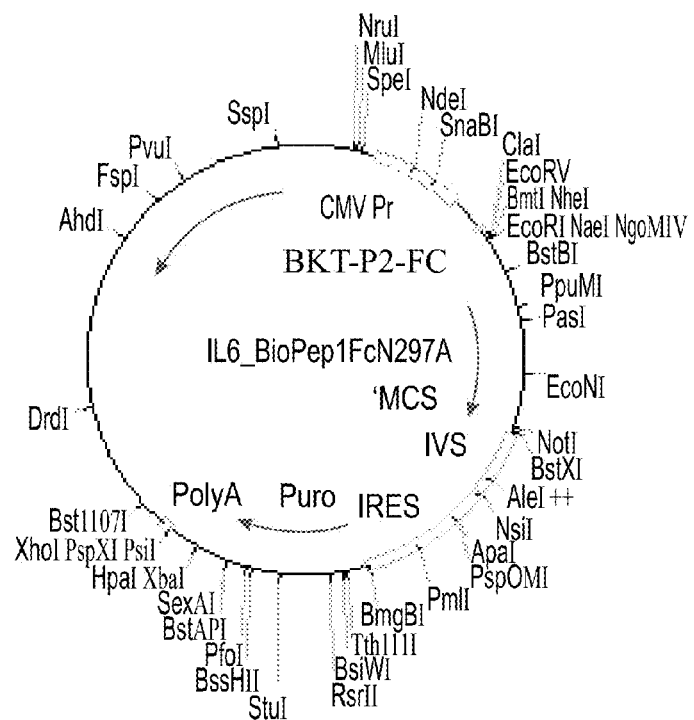
FIGS. 1A and 1B are vector maps of vectors used to encode polypeptides according to some embodiments of the invention, namely, SEQ ID NO: 158 (BKT-P2-FC.
Figure 1B:
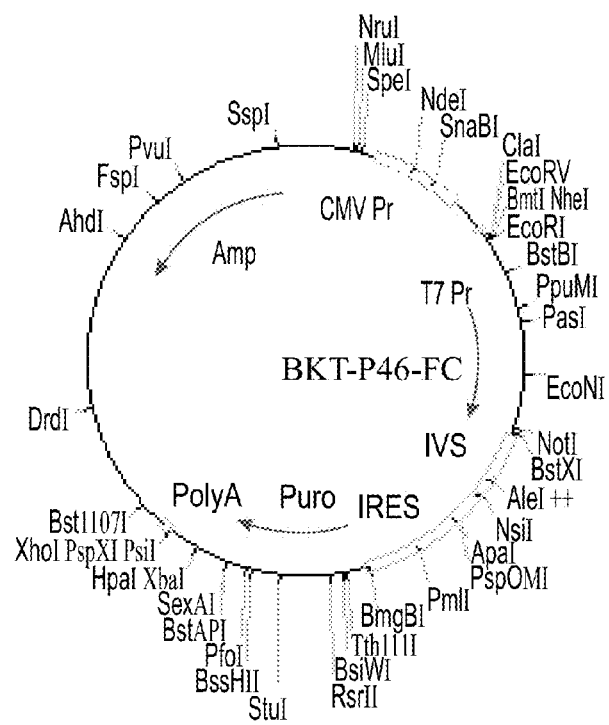
Figure 2:
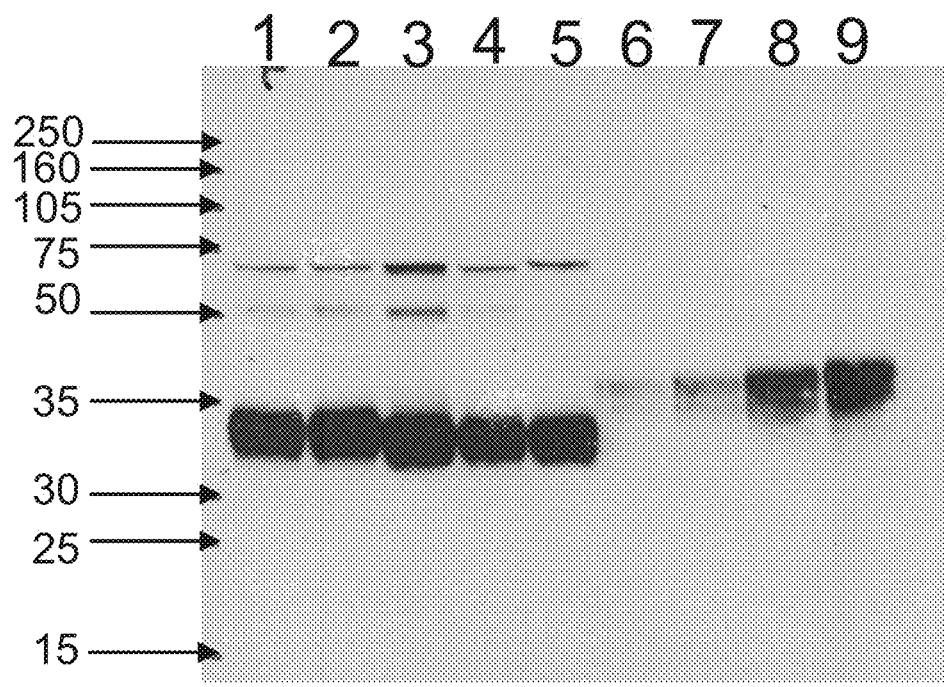
FIG. 2 is an image of a Western blot showing expression of IgG Fc in HEK 293T cell pools genetically engineered to produce the exemplary polypeptides SEQ ID NO: 158 (lanes 1 and 2) and SEQ ID NO: 159 (lanes 3-5), and 50 ng (lane 6), 100 ng (lane 7), 200 ng (lane 8) and 300 ng (lane 9) of control IgG Fc.

Referring now to the drawings and tables, FIGS. 1A and 1B illustrate exemplary DNA constructs used to express exemplary polypeptides, referred to herein as BKT-P2-FC (SEQ ID NO: 158) and BKT-P46-FC (SEQ ID NO: 159), according to some embodiments of the invention. FIG. 2 shows expression of the aforementioned exemplary polypeptides in a cell culture, as detected by Western blot.

"BKT-P2-FC" and "BKT-P46-FC" are trademarks owned by the owners of the present invention. BKT-P2-FC refers to a polypeptide also designated as "IL6 signal peptide-BKT-P2-Spacer-FC", "P2-Fc", "BKT-Fc-2", "BKT-Fc-P2", "IL6-P2-Fc", "IL6-P2-Fc N297A" and "IL6-BioPep1-Fc N297A" in Provisional Patent Application No. 61/213,493. BKT-P46-FC refers to a polypeptide also designated as "IL6 signal peptide-BKT-P46-Spacer-FC", "BKT-Fc-46", BKT- FC-46", "P46-FC", IL6-P46-Fc", "IL6-P46-Fc N297A" and "IL6-BioPep2-Fc N297A" in Provisional Patent Application No. 61/213,493.

Table 3 presents the dissociation constants for binding of the aforementioned exemplary polypeptides to a variety of chemokines.

Figure 3A:
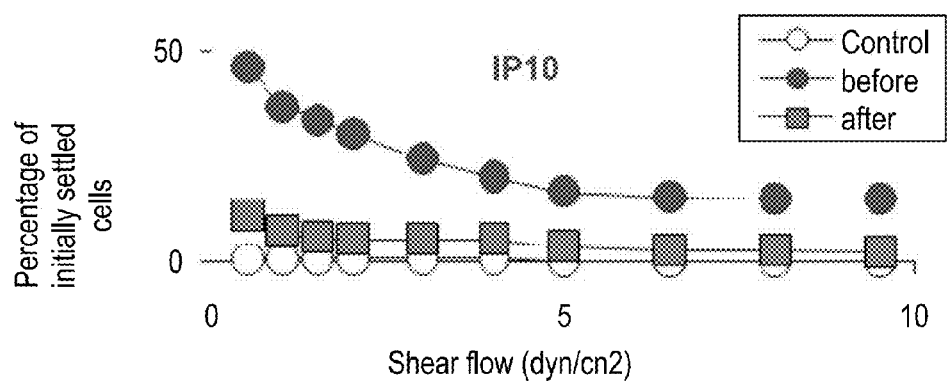
FIGS. 3A-3C are graphs showing T cell adhesion to VCAM-1 induced by IP-10 (FIG. 3A), I-TAC (FIG. 3B), and MIG (FIG. 3C) as a function of shear flow, before and after exposure to the peptide BKT-P2 (SEQ ID NO: 101) (T cell adhesion in the presence of a heat-inactivated SDF-1 cytokine is shown as a control.
Figure 3B:
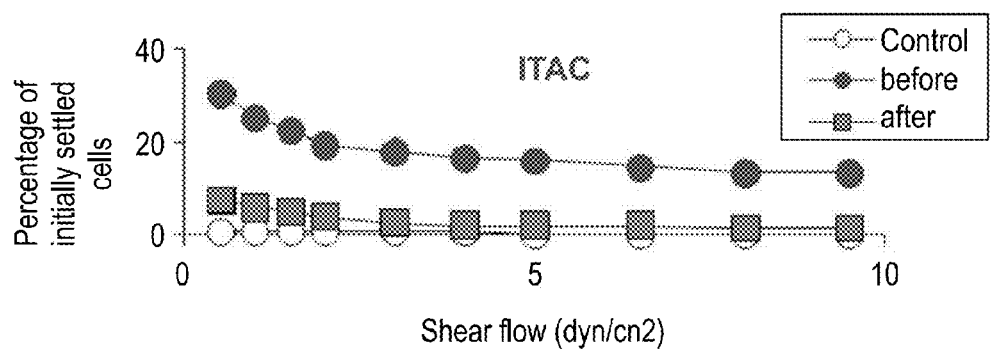
Figure 3C:
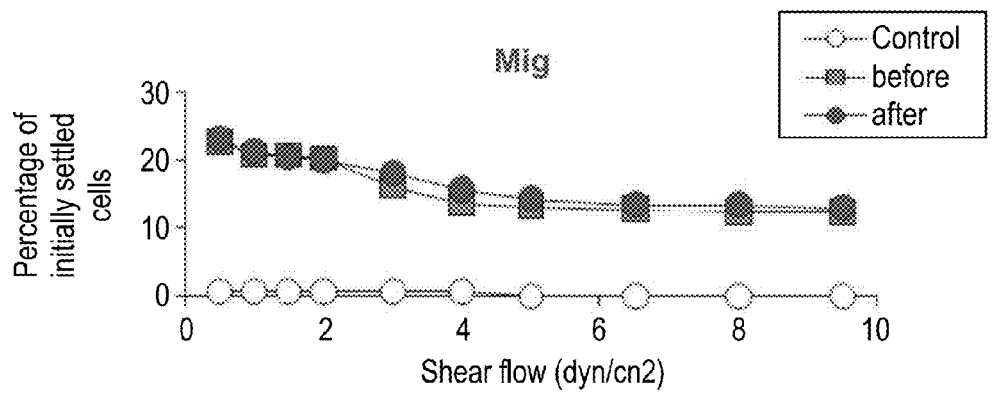
Figure 4A:
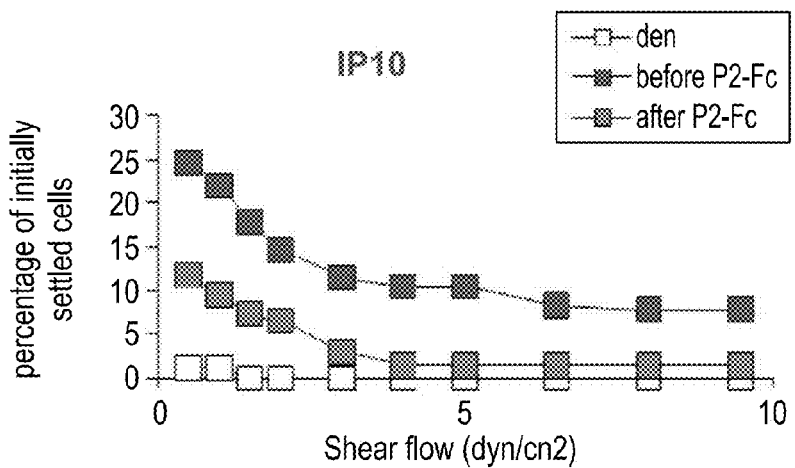
FIGS. 4A-4C are graphs showing T cell adhesion to VCAM-1 induced by IP-10 (FIG. 4A), I-TAC (FIG. 4B), and MIG (FIG. 4C) as a function of shear flow, before and after exposure to BKT-P2-FC (SEQ ID NO: 158), a polypeptide according to some embodiments of the invention (T cell adhesion in the presence of a heat-inactivated SDF-1 cytokine is shown as a control (den)
Figure 4B:
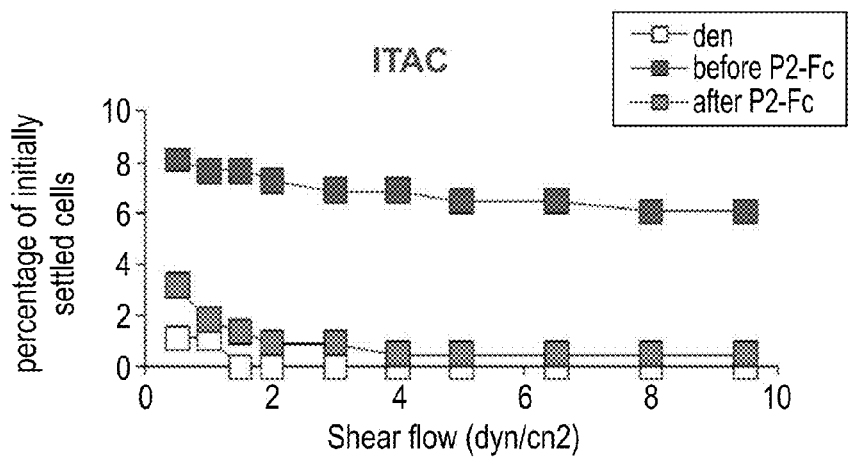
Figure 4C:
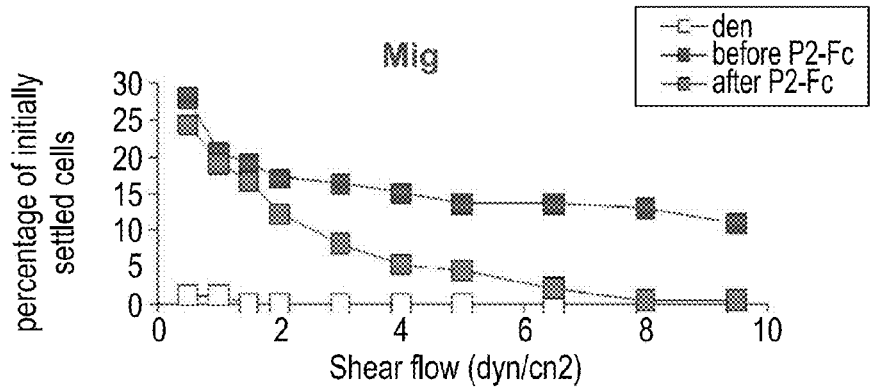

FIGS. 4A-4C show inhibition by an exemplary polypeptide (SEQ ID NO: 158) of a biological activity (induction of T cell adhesion) of some cytokines. For comparison, FIG. 3A-3C shows the inhibition of the same activity by a chemokine-binding peptide (SEQ ID NO: 101) upon which the polypeptide is based. Table 4 summarizes the ability of exemplary polypeptides (SEQ ID NO: 158 and SEQ ID NO: 159) and the chemokine-binding peptides upon which they are based (SEQ ID NO: 101 and SEQ ID NO: 76, respectively) to inhibit the activity of a variety of chemokines.

Figure 8A:
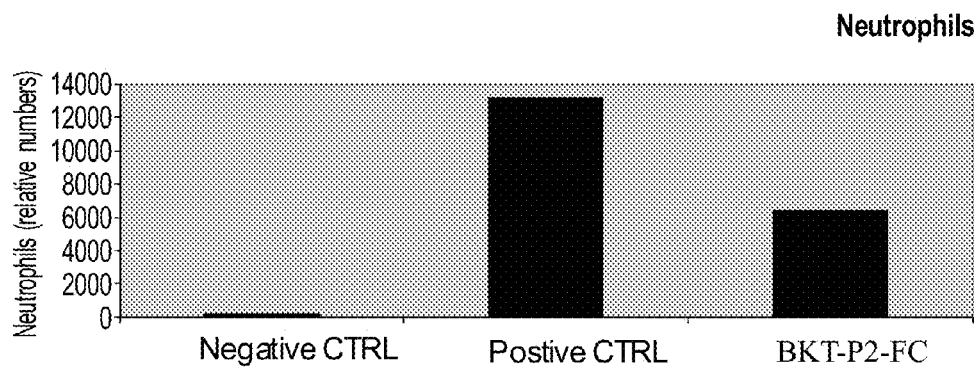
FIGS. 8A and 8B are graphs showing levels of neutrophils (FIG. 8A) and monocytes (FIG. 8B) in the knee cavity of healthy mice (Negative CTRL), arthritic mice (Positive CTRL) and arthritic mice treated with an exemplary polypeptide having SEQ ID NO: 158 (BKT-P2-FC)
Figure 8B:
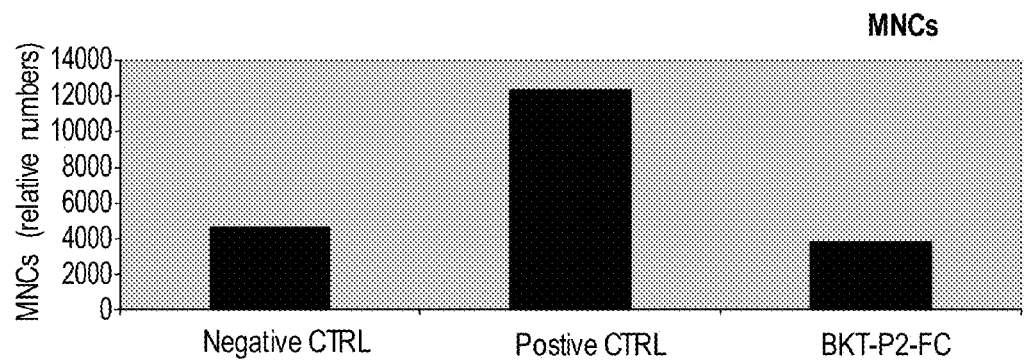
Figure 9:
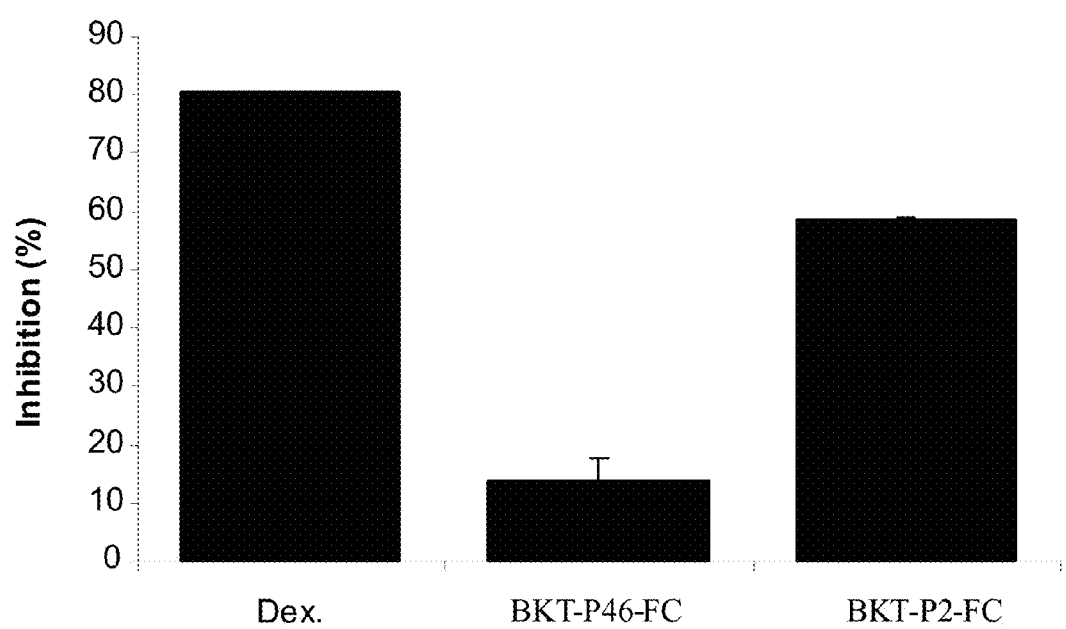
FIG. 9 is a graph showing inhibition of delayed type hypersensitivity by the exemplary polypeptides having SEQ ID NO: 159 (BKT-P46-FC) and SEQ ID NO: 158 (BKT-P2-FC) (inhibition by dexamethasone (Dex.) is shown for comparison).

FIGS. 5A, 5B, 6 and 7 show the efficacy of exemplary polypeptides according to some embodiments of the invention against progression of EAE (experimental autoimmune encephalomyelitis) in mice. FIGS. 8A and 8B shows the efficacy of an exemplary polypeptide against arthritis in mice. FIG. 9 shows the efficacy of exemplary polypeptides against delayed type hypersensitivity.

Table 5 presents chemokine-binding peptides which may be included in polypeptides according to embodiments of the present invention.

Thus, the experimental results presented herein show that polypeptides according to embodiments of the present invention are capable of binding to chemokines (see for example Table 3), are even more potent modulators of chemokine activity than are the corresponding chemokine-binding peptides (see for example Table 4 and FIGS. 3A, 3B, 4A and 4B), and are therapeutically effective for treating a variety of conditions (see for example FIGS. 5A-9).

Hence, according to an aspect of some embodiments of the invention, there is provided an isolated polypeptide comprising at least one chemokine-binding peptide attached to an Fc domain of an antibody (e.g., IgG, IgA, IgD, IgE, IgM antibodies) or a fragment of an Fc domain. Molecules comprising a peptide attached to an Fc domain or fragment thereof may be referred to herein as "peptibodies".

In some embodiments, the polypeptide comprises a single chemokine-binding peptide.

Alternatively, the polypeptide comprises more than one chemokine-binding peptide (e.g., 2, 3, 4 or 5 chemokine-binding peptides). The chemokine-binding peptides may the same as one another or may be different from one another.

As used herein, the term "chemokine-binding peptide" refers to any peptide (e.g., a peptide of up to 20 amino acid residues) characterized by an ability to bind to at least one chemokine in solution. Exemplary chemokines include, but are not limited to CCL1 (where CCL is short for Chemokine (C—C motif) ligand), MCP-1 (also referred to in the art as CCL2), MIP-1 (including MIP-1α and/or MIP-1β), RANTES (also referred to in the art as CCL5), CCL6, CCL7, CCL8, CCL9, eotaxin (also referred to in the art as CCL11), CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1 (where CXCL is short for Chemokine (C—X—C motif) ligand), CXCL2, CXCL3, CXCL4, CXCL5, CXCL6, CXCL7, interleukin-8 (also referred to in the art as CXCL8), MIG (also referred to in the art as CXCL9), IP-10 (also referred to in the art as CXCL10), I-TAC (also referred to in the art as CXCL11), SDF-1 (also referred to in the art as CXCL12), BCA-1 (also referred to in the art as CXCL13), CXCL14, CXCL15, CXCL16, CXCL17, XCL1, XCL2 and CX3CL1. According to one embodiment, the peptides bind to at least one chemokine selected from the group consisting of I-TAC (Interferon-inducible T-cell alpha chemoattractant), IP-10 (10 kDa Interferon-γ-induced protein), MIG (Monokine induced by gamma-interferon), MCP-1 (Monocyte chemotactic protein-1), eotaxin and RANTES (Regulated upon activation, normal T-cell expressed, and secreted).

Binding to a chemokine may be determined according to any suitable technique (e.g., ELISA) known in the art. Optionally, the binding is such that a dissociation constant ($K_d$) for binding of the peptide to a chemokine is less than $10^{-4}$ M, optionally less than $10^{-5}$M, and optionally less than $10^{-6}$M. Suitable techniques for determining a dissociation constant will be know to the skilled artisan.

Chemokine-binding peptides which may be used according to embodiments of the invention are described, for example, in International Patent Application PCT/IL03/00155 (published as WO 03/072599) and U.S. Pat. No. 7,488,717.

In some embodiments, the chemokine-binding peptide is from 5 to 50 amino acids in length, optionally from 5 to 40 amino acids in length, optionally from 5 to 30 amino acids in length, optionally from 7 to 20 amino acids in length, optionally from 9 to 20 amino acids in length, and optionally from 10 to 20 amino acids in length. According to exemplary embodiments, the chemokine binding peptide is about 12 amino acids in length.

Optionally, the chemokine-binding peptide is selected from the group consisting of SEQ ID NOs: 1 to 157.

In some embodiments, the chemokine-binding peptide is characterized by the presence of at least 2 histidine residues and an overall positive charge (e.g., positively charged amino acids outnumber negatively charged amino acids), wherein the peptide is composed primarily of the amino acids selected from the group consisting of H, S, A, L, I, K, R, T and P (e.g., at least 40%, and optionally at least 50% of the peptide consists of the aforementioned amino acids).

Examples of peptides having the aforementioned characteristics include, without limitation, SIFAHQTPTHKN (SEQ ID NO: 100), SIPSHSIHSAKA (SEQ ID NO: 101), SAISDHRAHRSH (SEQ ID NO: 96), SAGHIHEAHRPL (SEQ ID NO: 95), ACHASLKHRC (SEQ ID NO: 44), AHSLKSITNHGL (SEQ ID NO: 46), ESDLTHALHWLG (SEQ ID NO: 54), HSACHASLKHRC (SEQ ID NO: 69), WSAHIVPYSHKP (SEQ ID NO: 143), YATQHNWRLKHE (SEQ ID NO: 145), CAHLSPHKC (SEQ ID NO: 1), GVHKHFYSRWLG (SEQ ID NO: 61), HPTTPIHMPNF (SEQ ID NO: 66), SVQTRPLFHSHF (SEQ ID NO: 113), and VHTSLLQKHPLP (SEQ ID NO: 133). SIPSHSIH-SAKA (SEQ ID NO: 101), referred to herein as "BKT-P2", is an exemplary chemokine-binding peptide.

In some embodiments, the chemokine-binding peptide is characterized by the presence of at least two adjacent histidine residues and an overall positive charge (e.g., positively charged amino acids outnumber negatively charged amino acids), wherein the peptide is composed primarily of the amino acids selected from the group consisting of H, P, T, L, R, W and F (e.g., at least 40%, and optionally at least 50% of the peptide consists of the aforementioned amino acids).

Examples of peptides having the aforementioned characteristics include, without limitation, GDFNSGHHTTTR (SEQ ID NO: 59), HHFHLPKLRPPV (SEQ ID NO: 64), HHTWDTRIWQAF (SEQ ID NO: 65), LDYPIPQTVLHH (SEQ ID NO: 76), LLADTTHHRPWP (SEQ ID NO: 79), TRLVPSRYYHHP (SEQ ID NO: 125), CHHNLSWEC (SEQ ID NO: 7) and SFWHHHSPRSPL (SEQ ID NO: 99).

LDYPIPQTVLHH (SEQ ID NO: 76), referred to herein as "BKT-P46" is an exemplary chemokine-binding peptide.

Optionally, the chemokine binding peptide has an amino acid sequence showing at least 70%, at least 80%, at least 90% sequence homology to an amino acid sequence selected from the group consisting of SEQ ID NOs: 1 to 157 (e.g., SEQ ID NOs: 76 and 101). Optionally, the sequence homology is at least 95%. Optionally, the sequence homology is 100%.

Homology may be determined using BlastP software of the National Center of Biotechnology Information (NCBI) using default parameters. Homology may also refer to a deletion, insertion, or substitution variant, including an amino acid substitution thereof and biologically active polypeptide fragments thereof.

As used herein, an "Fc domain" refers to a region of a heavy chain of an antibody, typically comprising at least 2 constant domains (e.g., CH2 and CH3 domains, as these terms are defined in the art) of the heavy chain. The Fc domain may be obtained, for example, in the form of a dimer, by digestion of an antibody by papain. A dimer of Fc domain polypeptides, connected by disulfide bonds, forms the "tail" region of an antibody. As is known in the art, Fc domains of some classes of antibodies may be in the form of multimers. Thus, the Fc domain is optionally monomeric, optionally dimeric and optionally multimeric. Optionally, the polypeptide described herein is in the form of a dimer, the polypeptide comprising an Fc dimer, or in the form of a multimer, the polypeptide comprising an Fc multimer.

The Fc domain may encompasses modified forms of a native Fc domain (i.e., a domain which occurs naturally in an antibody), for example, polypeptides having at least 90% homology, optionally at least 95% homology, and optionally at least 98% homology, to a native Fc domain. Modified Fc domains are described, for example, in International Patent Applications WO 97/34631 and WO 96/32478.

Optionally, a native Fc is modified so as to remove sites which provide structural features or biological activity that are not required for embodiments of the present invention. Examples of such sites include residues that affect or are involved in disulfide bond formation, incompatibility with a selected host cell, N-terminal heterogeneity upon expression in a selected host cell, glycosylation, interaction with complement, binding to an Fc receptor (other than a neonatal Fc receptor), and/or antibody-dependent cellular cytotoxicity.

The polypeptide according to embodiments of the present invention may also comprise a fragment of an Fc domain. Optionally, the fragment comprises at least 20%, optionally at least 50%, and optionally at least 80% of an Fc domain, as defined hereinabove.

The Fc domain or fragment thereof optionally includes a binding site for a neonatal Fc receptor (FcRn).

As exemplified in the Examples section below, polypeptides according to embodiments of the present invention exhibited a relatively long lifetime in the blood circulation, with significant levels of polypeptide remaining in the blood at least 11 days after administration.

According to one embodiment, attachment of an Fc domain or a fragment thereof to the chemokine-binding peptide results in a polypeptide having a longer half-life in vivo than the chemokine-binding peptide per se. This may be due to the long serum half-life of the Fc domain (which may be due to salvage of the Fc via binding to FcRn) and/or due to the greater size of the polypeptide in comparison to the chemokine-binding peptide, which reduces clearance from the bloodstream by glomerular filtration. According to another embodiment, the resulting polypeptides have reduced immunogenicity as compared to the chemokine-binding peptide per se.

According to optional embodiments, the Fc domain or fragment thereof is a human Fc domain (e.g., derived from a human antibody) or fragment thereof.

According to exemplary embodiments, the Fc domain (or fragment thereof) is an IgG (e.g., IgG1) Fc domain (or fragment thereof). Optionally, the Fc domain or fragment is non-glycosylated.

According to exemplary embodiments, the Fc fragment has SEQ ID NO: 160, which corresponds to a human IgG1 Fc fragment with an N297A mutation.

Optionally, the N-terminus of the Fc domain (or fragment thereof) is attached, (directly or via a linker), to a chemokine-binding peptide. The N-terminus is optionally attached to more than one chemokine-binding peptide, for example, by being attached to a sequence which comprises more than one chemokine-binding peptide.

Alternatively or additionally, the C-terminus of the Fc domain (or fragment thereof) is attached, directly or via a linker (e.g., an amino acid linker), to a chemokine-binding peptide. The C-terminus is optionally attached to more than one chemokine-binding peptide.

In addition to the chemokine-binding peptide and the Fc domain or fragment described herein, the polypeptide described herein may further comprise one or more additional peptide sequences. Such sequences may optionally be selected so as to provide a desirable biological activity or structural feature, for example, an activity or feature which improves a therapeutic efficacy of the polypeptide or which facilitates production of the polypeptide.

Thus, for example, the polypeptide optionally comprises at least one signal peptide selected to be capable of directing transport of the polypeptide.

Optionally, the signal peptide is selected to be capable of promoting secretion of the polypeptide from a cell (e.g., a mammalian cell) expressing the polypeptide.

Optionally, a vacuolar signal sequence (for a polypeptide produced by plant transfection) is included In exemplary embodiments, the polypeptide comprises an IL-6 (interleukin-6) signal peptide (e.g., SEQ ID NO: 161) or a signal peptide that has an amino acid sequence showing at least 90% homology (optionally at least 95% homology) to an IL-6 signal peptide.

The abovementioned additional peptide sequence (e.g., signal peptide) may be present at the N-terminus of the polypeptide, the C-terminus of the polypeptide or in the middle of the polypeptide (e.g., between an Fc domain or fragment and a chemokine-binding peptide, or between two chemokine-binding peptides).

Thus, the Fc domain or fragment, the chemokine-binding peptide(s) and any additional peptide(s) (if present) described herein may be attached to one another within the polypeptide in any order.

The Fc domain or fragment, the chemokine-binding peptide(s) and any additional peptide(s) (if present) are independently attached to one another directly or via a linker (e.g., an amino acid linker).

However, the activity of some signal peptides depends on location at a particular location (e.g., N-terminus, C-terminus) within a polypeptide. Hence, according to some embodiments, a signal peptide is located at a particular location in the polypeptide.

According to exemplary embodiments, the signal peptide (e.g., an IL-6 signal peptide) is at the N-terminus of the polypeptide. Examples of polypeptides having a signal peptide at the N-terminus include polypeptides of the following formulas:

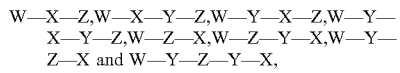

wherein W is a signal peptide, X is a chemokine-binding peptide, Y is a linker (e.g., amino acid linker) and Z is the Fc domain or fragment. According to exemplary embodiments, the polypeptide has the above formula W—X—Y—Z.

The linker (also referred to as a "spacer") is optionally an amino acid linker comprising an amino acid, a dipeptide, a tripeptide, or 4 or more amino acids. Such linkers are advantageous in that they allow the polypeptide to comprise a single contiguous polypeptide chain, which can be readily produced as a fusion protein. The linker is typically selected such that it does not interfere with binding of the chemokine binding peptide to its target chemokine. Optionally, the linker is a peptide composed of 4 to 10 amino acids (e.g., a hexapeptide). According to exemplary embodiments, the linker is a peptide set forth in SEQ ID NO: 162. In embodiments comprising more than one linker, the linkers may be the same or different from one another.

According to preferred embodiments of the invention, the polypeptide is capable of binding to at least one chemokine (e.g., via interaction of the chemokine-binding peptide in the polypeptide with the chemokine). Binding of a polypeptide to a chemokine will in many cases affect the ability of a chemokine (e.g., I-TAC, IP-10, MIG, MCP-1, eotaxin and/or RANTES) to bind to a chemokine receptor.

Hence, in some embodiments, the polypeptide is characterized by an ability to inhibit binding of at least one chemokine to a chemokine receptor. Optionally, the inhibition of binding is such that the dissociation constant (for binding of the chemokine to the receptor) in the presence of the polypeptide is at least 10%, and optionally at least 100%, higher than the dissociation constant in the absence of the polypeptide.

In some embodiments, the polypeptide is characterized by an ability to enhance binding of at least one chemokine to a chemokine receptor. Optionally, the enhancement of binding is such that the dissociation constant (for binding of the chemokine to the receptor) in the presence of the polypeptide is at least 10%, and optionally at least 50%, lower than the dissociation constant in the absence of the polypeptide.

It is to be appreciated that a polypeptide according to embodiments of the present invention may optionally inhibit binding of at least one chemokine to a chemokine receptor and also enhance binding of at least one other chemokine to a chemokine receptor.

The term "polypeptide" as used herein encompasses native polypeptides (e.g., degradation products, synthetically synthesized polypeptides or recombinant polypeptides) and peptidomimetics (typically synthetically synthesized), as well as peptoids and semipeptoids which are polypeptide analogs, which may have, for example, modifications rendering the polypeptides more stable while in a body or more capable of penetrating into cells. Such modifications include, but are not limited to N' terminus modification, C' terminus modification, polypeptide bond modification, including, but not limited to, CH2-NH, CH2-S, CH2-S═O, O═C—NH, CH2-O, CH2-CH2, S═C—NH, CH═CH or CF═CH, backbone modifications, and residue modifications. Methods for preparing peptidomimetic compounds are well known in the art and are specified, for example, in Quantitative Drug Design, C. A. Ramsden Gd., Chapter 17.2, F. Choplin Pergamon Press (1992).

Polypeptide bonds (—CO—NH—) within the polypeptide may be substituted, for example, by N-methylated bonds (—N(CH3)-CO—), ester bonds (—C(R)H—C—O—O—C(R)—N—), ketomethylene bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acids such as phenylglycine, 1,2,3,4-tetrahydroisoquinoline-3-carboxylic acid (TIC), naphthylalanine (Nal), ring-methylated derivatives of Phe, halogenated derivatives of Phe or o-methyl-Tyr.

The amino acid sequences of naturally occurring peptides and polypeptides described herein (e.g., Fc domain sequences, signal peptides) may either be the amino acid sequences of the polypeptides in naturally-occurring proteins or those that comprise either conservative or non-conservative substitutions.

The term "conservative substitution" as used herein, refers to the replacement of an amino acid present in the native sequence in the peptide with a naturally or non-naturally occurring amino acid or a peptidomimetic having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered conservative substitutions.

For producing conservative substitutions by non-naturally occurring amino acids it is also possible to use amino acid analogs (synthetic amino acids) well known in the art. A peptidomimetic of the naturally occurring amino acids is well documented in the literature known to the skilled practitioner.

When effecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or —NH—CH[(—CH$_2$)$_5$COOH]—CO— for aspartic acid. Those non-conservative substitutions which fall within the scope of the present invention are those which still constitute a peptide or polypeptide having an activity of the native peptide (e.g., Fc domain sequence, signal peptide).

As used herein in the specification and in the claims section below, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table I) and non-conventional or modified amino acids (Table II) which can be used with the present invention.

TABLE 1

| Amino Acid | Three-Letter Abbreviation | One-letter Symbol |
| --- | --- | --- |
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code |
| --- | --- |
| α-aminobutyric acid | Abu |
| α-amino-α-methylbutyrate | Mgabu |
| aminocyclopropanecarboxylate | Cpro |
| aminoisobutyric acid | Aib |
| aminonorbornylcarboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |

TABLE 2-continued

| Non-conventional amino acid | Code |
| --- | --- |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-α-methylalnine | Dnmala |
| D-α-methylarginine | Dnmarg |
| D-α-methylasparagine | Dnmasn |
| D-α-methylasparatate | Dnmasp |
| D-α-methylcysteine | Dnmcys |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α thylglutamine | Mgln |
| L-α-methylhistidine | Mhis |
| L-α-methylisoleucine | Mile |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-αethylhistidine | Mhis |
| L-αthylisoleucine | Mile |
| L-α-methylleucine | Mleu |
| L-α-methylmethionine | Mmet |
| L-α-methylnorvaline | Mnva |

TABLE 2-continued

| Non-conventional amino acid | Code |
|---|---|
| L-α-methylphenylalanine | Mphe |
| L-α-methylserine | mser |
| L-αethylvaline | Mtrp |
| L-α-methylleucine | Mval |
|  | Nnbhm |
| N-(N-(2,2-diphenylethyl) carbamylmethyl-glycine | Nnbhm |
| 1-carboxy-1-(2,2-diphenyl ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| αethylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododeclglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-indolylethyl) glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylserine | Dnmser |
| D-N-methylthreonine | Dnmthr |
| N-(1-methylethyl)glycine | Nva |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomo phenylalanine | Mhphe |
| N-(2-methylthioethyl)glycine | Nmet |
| N-(3-guanidinopropyl)glycine | Narg |
| N-(1-hydroxyethyl)glycine | Nthr |
| N-(hydroxyethyl)glycine | Nser |
| N-(imidazolylethyl)glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl(1)glycine | Nnbhe |

Recombinant techniques are preferably used to generate the polypeptides of the present invention since these techniques are better suited for generation of relatively long polypeptides (e.g., longer than 20 amino acids) and large amounts thereof. Such recombinant techniques are described by Bitter et al., (1987) *Methods in Enzymol.* 153:516-544, Studier et al. (1990) *Methods in Enzymol.* 185:60-89, Brisson et al. (1984) *Nature* 310:511-514, Takamatsu et al. (1987) *EMBO J.* 6:307-311, Coruzzi et al. (1984) *EMBO J.* 3:1671-1680, Brogli et al., (1984) *Science* 224:838-843, Gurley et al. (1986) *Mol. Cell. Biol.* 6:559-565 and Weissbach & Weissbach, 1988, *Methods for Plant Molecular Biology*, Academic Press, NY, Section VIII, pp 421-463.

To produce a polypeptide of the present invention using recombinant technology, a polynucleotide encoding a polypeptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

Examples of an isolated polynucleotide which can be used to express a chemokine-binding peptide are set forth in SEQ ID NOs: 163 and 164. An Example of isolated polynucleotide sequences which can be used to express an Fc fragment is as set forth in SEQ ID NO: 165. An example of an isolated polynucleotide which can be used to express an IL-6 signal peptide is set forth in SEQ ID NO: 166. An example of an isolated polynucleotide which can be used to express a linker is set forth in SEQ ID NO: 167.

Exemplary polynucleotide sequences which can be used to express a polypeptide according to some embodiments of the present invention are set forth in SEQ ID NO: 168 and 169.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein, the phrase "complementary polynucleotide sequence" refers to a sequence which results from reverse transcription of messenger RNA using a reverse transcriptase or any other RNA-dependent DNA polymerase. Such a sequence can be subsequently amplified in vivo or in vitro using a DNA-dependent DNA polymerase.

As used herein, the phrase "genomic polynucleotide sequence" refers to a sequence derived (isolated) from a chromosome and thus represents a contiguous portion of a chromosome.

As used herein, the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis-acting expression regulatory elements.

As mentioned, the polynucleotides of embodiments of the present invention may further comprise a signal sequence encoding a signal peptide (as discussed hereinabove) for the secretion of the polypeptide.

Following expression and secretion, the signal peptides are optionally removed from the precursor proteins resulting in the mature polypeptide.

Polynucleotides of the present invention may be prepared using PCR techniques as described, for example, in Example 1 herein below, or any other method or procedure known in the art for ligation of two different DNA sequences. See, for example, "Current Protocols in Molecular Biology", eds. Ausubel et al., John Wiley & Sons, 1992.

As mentioned hereinabove, polynucleotide sequences of the present invention are typically inserted into expression vectors (i.e., a nucleic acid construct) to enable expression of the recombinant polypeptide. The expression vector of embodiments of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000-fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pIRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed.

Recombinant viral vectors may be useful for expression of the polypeptides of embodiments of the present invention since they offer advantages such as lateral infection. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

A variety of prokaryotic or eukaryotic cells can be used as host-expression systems to express the polypeptides of the present invention. These include, but are not limited to, microorganisms, such as bacteria (for example, *E. coli* including but not limited to *E. coli* strains BL21 (DE3) plysS, BL21; (DE3)RP and BL21* and *B. subtilis*) transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

Various methods can be used to introduce the expression vector of the present invention into the cells of the host expression system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Nucleic acid sequences of the polypeptides of the present invention may be optimized for expression in a particular host cell. Examples of such sequence modifications include, but are not limited to, an altered G/C content to more closely approach that typically found in the species of interest, and the removal of codons atypically found in the species commonly referred to as codon optimization.

The phrase "codon optimization" refers to the selection of appropriate DNA nucleotides for use within a structural gene or fragment thereof that approaches codon usage within the species of interest. Therefore, an optimized gene or nucleic acid sequence refers to a gene in which the nucleotide sequence of a native or naturally occurring gene has been modified in order to utilize statistically-preferred or statistically-favored codons within the selected species. The nucleotide sequence typically is examined at the DNA level and the coding region optimized for expression in the species determined using any suitable procedure, for example as described in Sardana et al. (1996, *Plant Cell Reports* 15:677-681). In this method, the standard deviation of codon usage, a measure of codon usage bias, may be calculated by first finding the squared proportional deviation of usage of each codon of the native gene relative to that of highly expressed genes of the selected species, followed by a calculation of the average squared deviation. The formula used is: 1 SDCU=n=1 N [(Xn−Yn)/Yn]2/N, where Xn refers to the frequency of usage of codon n in highly expressed genes, where Yn to the frequency of usage of codon n in the gene of interest and N refers to the total number of codons in the gene of interest.

One method of optimizing the nucleic acid sequence in accordance with the preferred codon usage for a particular cell type is based on the direct use, without performing any extra statistical calculations, of codon optimization tables such as those provided on-line at the Codon Usage Database through the NIAS (National Institute of Agrobiological Sciences) DNA bank in Japan (www.kazusa.or.jp/codon/). The Codon Usage Database contains codon usage tables for a number of different species, with each codon usage table having been statistically determined based on the data present in Genbank.

By using the above tables to determine the most preferred or most favored codons for each amino acid in a particular species, a naturally-occurring nucleotide sequence encoding a protein of interest can be codon optimized for that particular species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular species. Therefore, codon optimization of the native nucleotide sequence may comprise determining which codons, within the native nucleotide sequence, are not statistically-favored with regards to a particular species, and modifying these codons in accordance with a codon usage table of the particular species to produce a codon optimized derivative. A modified nucleotide sequence may be fully or partially optimized for codon usage in a particular species, provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus, the present invention encompasses nucleic acid sequences described hereinabove; fragments thereof, sequences hybridizable therewith, sequences homologous thereto, sequences orthologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Independent of the host cell system, it will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, resultant polypeptides of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

The polypeptides of embodiments of the present can be conveniently purified by affinity chromatography. The suitability of protein A as an affinity ligand depends on the species and isotype of the immunoglobulin Fc domain that is used in the chimera. Protein A can be used to purify chimeric molecules that are based on human γ1, γ2, or γ4 heavy chains [Lindmark et al., J. Immunol. Meth., 62:1-13 (1983)]. Protein G is preferably used for all mouse isotypes and for human γ3 [Guss et al., EMBO J., 5:1567-1575 (1986)]. The solid support to which the affinity ligand is attached is most often agarose, but other solid supports are also available. Mechanically stable solid supports such as controlled pore glass or poly(styrenedivinyl)benzene allow for faster flow rates and shorter processing times than can be achieved with agarose. The conditions for binding the chimeric molecules to the protein A or G affinity column are dictated entirely by the characteristics of the Fc domain; that is, its species and isotype. Generally, when the proper ligand is chosen, efficient binding occurs directly from unconditioned culture fluid. Bound polypeptides of this aspect of the present invention can be efficiently eluted either at acidic pH (at or above 3.0), or in a neutral pH buffer containing a mildly chaotropic salt. This affinity chromatography step can result in polypeptide preparation that is >95% pure.

Other methods known in the art can be used in place of, or in addition to, affinity chromatography on protein A or G to purify the polypeptides of embodiments of the present invention. For example, it is anticipated that the polypeptides may behave similarly to antibodies in thiophilic gel chromatography [Hutchens et al., Anal. Biochem., 159:217-226 (1986)] and immobilized metal chelate chromatography [Al-Mashikhi et al., J. Dairy Sci., 71:1756-1763 (1988)].

To facilitate recovery, the expressed coding sequence can be engineered to encode the polypeptide of the present invention and fused cleavable moiety e.g. histidine. Such a fusion protein can be designed so that the polypeptide can be readily isolated by affinity chromatography; e.g., by immobilization on a column specific for the cleavable moiety.

Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The polypeptide of the present invention is preferably retrieved in a "substantially pure" form.

As used herein, the phrase "substantially pure" refers to a purity that allows for the effective use of the polypeptide in the applications described herein.

In addition to being synthesizable in host cells, the polypeptide of the present invention can also be synthesized using in vitro expression systems. These methods are well known in the art and the components of the system are commercially available.

The polypeptide may be used as is, or further modified.

For example, the polypeptide may be modified by attaching a water-soluble polymer (e.g., polyethylene glycol) to the polypeptide. Such an attachment of a water-soluble polymer may improve a biological activity of the polypeptide, for example, by increasing a solubility of the polypeptide, reducing a toxicity of the polypeptide, extending the circulation half-life of the polypeptide (e.g., by reducing glomerular filtration), and/or protecting the polypeptide from proteolytic degradation.

Hence, according to optional embodiments of the present invention, the polypeptide described herein is attached to a water-soluble polymer. Polyethylene glycol is a suitable water-soluble polymer. Additional water-soluble polymers suitable (e.g., non-toxic) for attaching to a polypeptide intended for pharmaceutical administration will be apparent to one of skill in the art.

The water-soluble polymer may be attached to any part of the polypeptide (directly or via a linker). Optionally, the water-soluble polymer is attached to a part of the polypeptide other than the chemokine-binding peptide, so as not to interfere with the chemokine-binding activity thereof.

As described herein and exemplified in the Examples section below, polypeptides described herein are effective at modulating an activity of a chemokine, which may have numerous advantageous therapeutic applications. Thus, novel and efficient methods for modulating chemokine activity and/or treating a variety of medical conditions are provided herein.

Accordingly, in one aspect of embodiments of the invention there is provided a method of modulating a biological effect of a chemokine (e.g., I-TAC, IP-10, MIG, MCP-1, eotaxin and/or RANTES), the method comprising administering a therapeutically effective amount of a polypeptide described herein (e.g., a modified or non-modified polypeptide described herein) to a subject in need thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As demonstrated in the Examples herein below, the polypeptides described herein can be for treating a variety of medical conditions. Treating the condition is effected by a method comprising administering a polypeptide described herein (e.g., a modified or non-modified polypeptide described herein) to a subject in need thereof. Examples of conditions which can be treated according to embodiments of the invention include, without limitation, an inflammation, an allergy, delayed type hypersensitivity, a non-optimal immune response, abnormal cell migration, an autoimmune reaction, rheumatoid arthritis, systemic lupus erythematosis, multiple sclerosis, an allograft rejection, diabetes, sepsis, cancer, a malignant cell growth, a bacterial infection, a viral infection, arthritis, colitis, psoriasis, atherosclerosis, hypertension, myasthenia gravis and reperfusion ischemia.

Optionally, administration comprises intravenous administration, oral administration, sub-cutaneous administration, topical administration and/or intranasal administration.

It will be appreciated that the Fc domain or fragment of polypeptides described herein may result in a longer half-life of the polypeptide in circulation, as compared to the half-life of the chemokine-binding peptide per se. Due to the longer half-life, therapeutically effective levels of the polypeptide can be maintained in vivo with less frequent administrations.

Hence, according to some embodiments, administration is effected no more than once per week, optionally no more than twice per month, optionally no more than once per month, optionally no more than once per two months, optionally no more than once per three months, and optionally no more than once per six months.

In alternative embodiments, a single administration is sufficient to achieve the desired therapeutic effect.

Similarly, according to an aspect of some embodiments of the present invention there is provided a use of a polypeptide as described herein (e.g., a modified or non-modified polypeptide described herein) in the manufacture of a medicament for modulating (e.g., inhibiting and/or enhancing, as described herein) a biological effect of a chemokine (e.g., I-TAC, IP-10, MIG, MCP-1, eotaxin and/or RANTES).

According to an aspect of some embodiments of the invention, there is provided a use of a polypeptide described herein (e.g., a modified or non-modified polypeptide described herein) in the manufacture of a medicament for treating a condition selected from the group consisting of an inflammation, an allergy, delayed type hypersensitivity, a non-optimal immune response, abnormal cell migration, an autoimmune reaction, rheumatoid arthritis, systemic lupus erythematosis, multiple sclerosis, an allograft rejection, diabetes, sepsis, cancer, a malignant cell growth, a bacterial infection, a viral infection, arthritis, colitis, psoriasis, atherosclerosis, hypertension, myasthenia gravis and reperfusion ischemia.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The subject to be treated may be human or a non-human animal. Preferably, the subject is a mammal. In some embodiments, the subject is human.

Treatments utilizing a polypeptide, as described herein, may be provided alone or together with other agents known to be useful in treating a particular disease. Medicaments and pharmaceutical compositions described herein may optionally further comprise one or more such agents.

Optionally, the medicament described herein is formulated for intravenous, oral, sub-cutaneous, topical administration and/or intranasal administration.

Examples of biological effects of a chemokine which can be modulated according to embodiments of the invention described herein include, without limitation, an inflammatory effect, cell migration, tumor growth and cancer metastasis.

In any aspect of the invention described herein, modulating a biological effect may comprise inhibiting or enhancing a biological effect. In exemplary embodiments, modulating comprises inhibiting. Optionally, a biological effect of at least one chemokine is inhibited, and a biological effect of another chemokine is enhanced.

In any of the methods and uses described herein, the polypeptide can be used either per se, or, preferably, as a part of a pharmaceutical composition which further comprises a pharmaceutically acceptable carrier.

Thus, according to an aspect of some embodiments of the present invention there is provided a pharmaceutical composition which comprises a polypeptide as described herein and a pharmaceutically acceptable carrier.

In some embodiments, the composition is packaged in a packaging material, and identified in print, in or on the packaging material, for use in modulating a biological effect of a chemokine (e.g., I-TAC, IP-10, MIG, MCP-1, eotaxin and/or RANTES), as described herein In some embodiments, the composition is packaged in a packaging material, and identified in print, in or on the packaging material, for use in the treatment of a condition selected from the group consisting of an inflammation, an allergy, delayed type hypersensitivity, a non-optimal immune response, abnormal cell migration, an autoimmune reaction, rheumatoid arthritis, systemic lupus erythematosis, multiple sclerosis, an allograft rejection, diabetes, sepsis, cancer, a malignant cell growth, a bacterial infection, a viral infection, arthritis, colitis, psoriasis, atherosclerosis, hypertension, myasthenia gravis and reperfusion ischemia.

The polypeptides described herein can be administered or otherwise utilized in the various aspects of the present invention, either as is or as a pharmaceutically acceptable salt thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

Suitable routes of administration may, for example, include the inhalation, oral, buccal, rectal, transmucosal, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes; and/or the route of direct injection into a tissue region of a subject. In optional embodiments, intravenous routes, oral routes, subcutaneous routes, topical routes and/or intranasal routes are used.

For skin diseases and disorders (e.g., psoriasis, skin allergies, skin hypersensitivity), topical administration is optionally used, for example, using a cream, a lotion, a gel or a powder formulated for topical administration.

The methods, compositions and uses described herein utilize the polypeptide in a therapeutically effective amount. Determination of a therapeutically effective amount is well within the capability of those skilled in the art.

For any preparation used in the methods and uses of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Dosing can be of a single administration or a plurality of administrations, as described herein.

Pharmaceutical compositions comprising one or more polypeptides as described herein may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with embodiments of the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients may be formulated in aqueous solutions, preferably in physiologically compatible buffers such as Hank's solution, Ringer's solution, or physiological salt buffer.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

A preparation according to embodiments of the present invention may also be formulated in rectal compositions such as suppositories or retention enemas, using, e.g., conventional suppository bases such as cocoa butter or other glycerides.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise glass, plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Polypeptides described herein are capable of binding to chemokines, and thus have a structure complementary to the structure of at least some chemokines. As chemokine receptors also have structures complementary to chemokines, it is expected that the structure of at least some polypeptides described herein bears a significant resemblance to a structure of a chemokine receptor. The polypeptide can therefore be used in some applications as a replacement for a chemokine receptor, for example, when generating an antibody capable of binding to a chemokine receptor.

Hence, in another aspect of embodiments of the invention, there is provided an antibody capable of recognizing at least a portion of a chemokine receptor. The antibody is optionally generated by producing an antibody against a polypeptide described herein, using standard techniques for producing an antibody.

Also provided herein is a vaccine comprising a polypeptide described herein, for producing auto-antibodies. The vaccine is designed so as to produce antibodies in a subject against the polypeptide, wherein the antibodies will further recognize and bind to at least a portion of at least one chemokine receptor in the subject. The vaccine optionally includes any suitable vaccine carrier that could easily be selected by one of ordinary skill in the art, including but not limited to, adjuvants, carriers and the like.

General methods to prepare immunogenic or vaccine compositions are described in Remington's Pharmaceutical Science; Mack Publishing Company Easton, Pa. (latest edition). To increase immunogenicity, the polypeptides of the present invention may be adsorbed to or conjugated to beads such as latex or gold beads, ISCOMs, and the like. Immunogenic compositions may comprise adjuvants, which are substance that can be added to an immunogen or to a vaccine formulation to enhance the immune-stimulating properties of the immunogenic moiety. Liposomes are also considered to be adjuvants (Gregoriades, G. et al., Immunological Adjuvants and Vaccines, Plenum Press, New York, 1989). Examples of adjuvants or agents that may add to the effectiveness of polypeptidic immunogens include aluminum hydroxide, aluminum phosphate, aluminum potassium sulfate (alum), beryllium sulfate, silica, kaolin, carbon, water-in-oil emulsions, and oil-in-water emulsions. A preferred type of adjuvant is muramyl dipeptide (MDP) and various MDP derivatives and formulations, e.g., N-acetyl-D-glucosaminyl-(β-1-4)-N-acetylmuramyl-L-alanyl-D-isoglutamine (GMDP) (Hornung, R L et al. Ther Immunol 1995 2:7-14) or ISAF-1 (5% squalene, 2.5% pluronic L121, 0.2% Tween 80 in phosphate-buffered solution with 0.4 mg of threonyl-muramyl dipeptide; see Kwak, L W et al. (1992) N. Engl. J. Med., 327:1209-1238). Other useful adjuvants are, or are based on, cholera toxin, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives such as QS21 (White, A. C. et al. (1991) Adv. Exp. Med. Biol., 303:207-210), which is now in use in the clinic (Helling, F et al. (1995) Cancer Res., 55:2783-2788; Davis, T A et al. (1997) Blood, 90: 509), levamisole, DEAE-dextran, blocked copolymers or other synthetic adjuvants. A number of adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.), Amphigen (oil-in-water), Alhydrogel (aluminum hydroxide), or a mixture of Amphigen and Alhydrogel. Aluminum is approved for human use.

As used herein the term "about" refers to ±10%.

The terms "comprises", "comprising", "includes", "including", "having" and their conjugates mean "including but not limited to".

The term "consisting of" means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral within the indicated range. The phrases "ranging/ranges between" a first indicate number and a second indicate number and "ranging/ranges from" a first indicate number "to" a second indicate number are used herein interchangeably and are meant to include the first and second indicated numbers and all the numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:
Amplification buffer (×10) was obtained from Invitrogen;
Dextran T-500 was obtained from Pharmacosmos A/S (Denmark);
Dulbecco's modified Eagle medium (DMEM) was obtained from Biological Industries (Beit Haemek, Israel);
ECL solution was obtained from Amersham Biosciences;
EcoRI was obtained from New England Biolabs;
Enhancer solution (×10) was obtained from Invitrogen;
Eotaxin (human) was obtained from PeproTech (Rocky Hill, N.J., USA);
EX-CELL® 293 medium was obtained from SAFC Biosciences;
Fetal calf serum (FCS) was obtained from Biological Industries (Beit Haemek, Israel);
Ficoll 1077 was obtained from Sigma;
Freund's complete adjuvant was obtained from Sigma or Difco;
FuGENE® 6 was obtained from Roche;
IP-10 (human) was obtained from PeproTech;
IL-8 (human) was obtained from PeproTech;
I-TAC (human) was obtained from PeproTech;
MCP-1 (human) was obtained from PeproTech;
Methylated bovine serum albumin (mBSA) was obtained from Sigma;
MIG (human) was obtained from PeproTech;
NotI was obtained from New England Biolabs;
NuPAGE® Bis Tris gels were obtained from Invitrogen;
pIRESpuro3 vector was obtained from BD Biosciences Clontech;
Protein A-Sepharose® beads were obtained from Amersham;
RANTES (human) was obtained from PeproTech;
RPMI medium was obtained from Biological Industries (Beit Haemek, Israel);
SDF-1α (human) was obtained from PeproTech;
Taq polymerase (Platinum® Pfx DNA polymerase) was obtained from Invitrogen; and
VCAM-1 (human) was obtained from R&D Systems, Inc. (Minneapolis, Minn.).
All chemokines were prepared according to the supplier's recommendations.

Two-Step PCR for Obtaining IL6-BKT Peptide DNA Fragments:
In the first PCR step, the IL6 signal peptide DNA sequence (SEQ ID NO: 166) was added to the DNA sequence corresponding to the first 9 amino acids of each BKT peptide. The product of this PCR reaction was used in the second PCR step as a template to add a DNA sequence corresponding to the remaining 3 amino acids of the BKT peptide, a spacer sequence (SEQ ID NO: 167), and a BstBI restriction site in the 3' end.

IL6-Fc pIRES puro DNA served as a DNA template for all three PCR reactions of the first PCR step. All three PCR reactions were done using the same forward primer (T7 primer; SEQ ID NO: 170). Using the universal T7 primer resulted in a PCR product which contained multiple cloning sites at the 5' end, including an NheI site, which was used later on for subcloning. The reverse primers were specific for each peptide; SEQ ID NO: 171 was used for BKT-P2 and SEQ ID NO: 172 was used for BKT-P46.

The PCR reaction conditions were as follows: 20 ng DNA template; 5 µl amplification ×10 buffer; 0.2 mM of each deoxyribonucleotide (dNTP); 0.5 mM MgSO$_4$; 5 µl enhancer solution ×10; 0.2 µM of each primer; 2.5 units of Taq polymerase; with water added to a total reaction volume of 50 µl.

Amplification was performed with an initial denaturation step at 94° C. for 3 minutes followed by 30 cycles of 94° C. for 30 seconds, 52° C. for 30 seconds, and 72° C. for 30 seconds, and then 10 minutes at 72° C.

At the end of the PCR amplification, 5 µl of each reaction mixture was analyzed on 2% agarose gels stained with ethidium bromide and visualized with UV light.

The PCR products of obtained by the above procedures were used as templates for the second PCR step. The abovementioned T7 primer was used as the forward primer in all three reactions, while the reverse primer was specific for each peptide; SEQ ID NO: 173 was used for BKT-P2 and SEQ ID NO: 174 was used for BKT-P46. Each reverse primer encoded amino acids 10-12 of the desired peptide and a hexapeptide spacer sequence (SEQ ID NO: 162), and included a BstB1 restriction site.

PCR reaction conditions were as follows: 0.5 µl of the DNA template; 5 µl amplification ×10 buffer; 0.2 mM of each dNTP; 0.5 µM MgSO$_4$; 5 µl enhancer solution ×10; 0.2 µM of each primer; 2.5 units of Taq polymerase; with water added to a total reaction volume of 50 µl.

Amplification and analysis of PCR products was performed as described above for the first PCR step. The PCR products were extracted from gel using a QiaQuick™ gel extraction kit (Qiagen™)

Ligation of IL6-BKT Peptide DNA Fragments to Fc Sequence:
The extracted IL6-BKT peptide DNA products were digested with NheI and BstBI, purified from an agarose gel as detailed above, and ligated into Fc N297A pIRESpuro3, previously digested with the same enzymes. The maps of the vectors for encoding SEQ ID NOs: 158 and 159 are shown in FIGS. 1A and 1B, respectively. The ligation mixture was transformed into DH5a competent cells. Ampicillin-resistant transformants were screened and positive clones were further analyzed by colony PCR.

DNA was extracted from the ampicillin-resistant colonies, and was subjected to two hours digestion at 37° C. with EcoRI and NotI restriction enzymes. The reaction was resolved on agarose gel. Positive colonies were expected to yield two bands of 5123 bp and 868 bp. The positive colonies were verified by DNA sequencing.

Western Blot:
The medium from a cell sample was collected and centrifuged (1000 rotations per minute, 7 minutes). 1 ml of the cell-deprived medium was incubated with 50 µl Protein A-Sepharose® beads for 45 minutes at room temperature. At the end of incubation time, proteins were eluted from the beads with 50 µl sample buffer containing 100 mM citrate phosphate buffer (pH 3.5) and 10 mM DTT (dithiothreitol). The samples were boiled for 3 minutes, and 25 µl of the sample were then loaded on a 12% NuPAGE® Bis Tris gel. The proteins were transferred to a nitrocellulose membrane and blocked with 10% low fat milk in PBST (PBS supplemented with 0.05% Tween-20). The membrane was then blotted for 1 hour with human anti-IgG Fc fragment antibody followed by goat anti-human antibody conjugated to HRP (horseradish peroxidase), at concentrations of 1:40,000 in blocking solution at room temperature. Following incubation with ECL solution, the membrane was exposed to film.

Surface Plasmon Resonance (SPR):

In a chamber that is covered with carboxymethyldextran, a peptide or polypeptide was covalently bound to the chamber, typically via the amine group of a lysine residue or the N-terminus. The chemokine was injected in increasing concentrations through the chamber.

Changes in light reflected from the surface are proportional to the amount of bound protein, and are detected by a detector.

Plotting the amount of protein bound at different concentrations of chemokine enabled the calculation of the dissociation coefficient.

T-Cell Purification from Fresh Blood:

50 ml of blood was added to 10 ml of a solution of Dextran T-500 (6% w/v) in PBS (phosphate buffer saline), and 7 ml of citrate buffer (25 grams citrate, 8 grams citric acid in 500 ml PBS). The solution was incubated for 30 minutes at 25° C. 10 ml of Ficoll 1077 was added to the bottom of the tube. The tube was then centrifuged at 2,000 rotations per minute for 30 minutes at 18° C. (with the brake mode of the centrifuge off). The interphase was collected and washed twice with 8 ml PBS with 5% FCS (fetal calf serum), followed by centrifugation at 1,400 rotations per minute for 5 minutes at 18° C. The cells were re-suspended in PBS with 5% FCS at a concentration less then $10^8$ per ml. 2 ml of the cell solution were applied on a poly(methyl methacrylate) nylon wool column which was pre-soaked in PBS-5% FCS, and then incubated for 45 minutes at 25° C. Each column was washed with 8 ml PBS-5% FCS and the cells (T-cells and erythrocytes) were eluted by 50 ml of 5 mM EDTA (ethylenediaminetetraacetic acid) in PBS. A red pellet was obtained by centrifugation at 1,400 rotations per minute for 5 minutes at 4° C. (with the brake on).

In order to perform lysis of the erythrocytes, the red pellet was re-suspended in 5 ml of lysis-buffer (155 mM $NH_4Cl$, 10 mM $KHCO_3$, 0.1 mM EDTA, X0.1 PBS) for 4 minutes, followed by immediate addition of 50 ml of PBS with EDTA. Following centrifugation at 1,400 rotations per minute for 5 minutes at 4° C., the pellet was washed again with 50 ml PBS-EDTA and re-centrifuged under the same conditions. A white pellet was obtained and re-suspended in RPMI medium with 10% FCS, L-glutamine, sodium pyruvate and antibiotics at a concentration of $3\times10^6$ cells per ml. The cells were incubated for 2 hours at 37° C., followed by collection of the non-adherent cells. The cells were ready for use in experiments after overnight incubation at 37° C.

In Vitro T Cell Adhesion Assay:

10 µg/ml of human VCAM-1 and 2 µg/ml of a chemokine (intact MIG, IP-10, I-TAC, MCP-1, RANTES, SDF-1 (stromal cell-derived factor-1), BCA-1 (B lymphocyte chemoattractant-1), IL-8 (interleukin-8) or eotaxin, or heat-inactivated SDF-1 as a control) were dissolved in PBS buffered with 20 mM bicarbonate (pH 8.5), and incubated in polystyrene plates overnight at 4° C. Alternatively, 10 µg/ml of the chemokine was used, and the plates were incubated for 30 minutes at room temperature. The plates were then washed three times and blocked by being incubated with 20 mg/ml human serum albumin in PBS for 2 hours at 37° C.

The plates were then assembled as the lower wall of a parallel wall flow chamber and mounted on the stage of an inverted microscope. 10 µg/ml of the peptide being tested was allowed to settle on the substrate-coated chamber wall for 10 minutes at 37° C. and was then washed. T cells were purified from fresh blood as described hereinabove ($5\times10^6$ per ml, purity >98%) and were suspended in binding buffer, perfused into the chamber, and allowed to settle on the substrate-coated chamber wall for 1 minute at 37° C. Flow was initiated and increased in 2 to 2.5 fold increments every 5 seconds, generating controlled shear stresses on the wall. Cells were visualized in a 20× objective of an inverted phase-contrast Diaphot Microscope (Nikon) and photographed with a long integration LIS-700 CCD video camera (Applitech; Israel), connected to a AG-6730 S-VHS video recorder (Panasonic). The number of adherent cells resisting detachment by the elevated shear forces was determined after each interval by analysis of videotaped cell images, and was expressed as the percent of originally settled cells. All adhesion experiments were performed at least three times on multiple test fields.

Experimental Autoimmune Encephalomyelitis (EAE):

EAE was induced in Female SJL and C57BL/6 mice. Mice were immunized subcutaneously in the flanks (day 0) with 100 µg $PLP_{139-151}$ peptide or 250 µg $MOG_{35-55}$ peptide, respectively. PLP and MOG peptides were emulsified in an equal volume of complete Freund's adjuvant (CFA) containing 800 µg *Mycobacterium tuberculosis* H37RA (Difco, Detroit, Mich.). Mice were also injected intraperitoneally with 300 ng pertussis toxin on days 0 and 2.

Mice were intravenously injected with BKT-P2-FC or BKT-P46-FC (50 µg/mouse) on day 9 post-immunization. In some experiments mice were treated at the peak of the disease, 14 days after disease induction, when the mice were intravenously injected with BKT-P2-FC or BKT-P46-FC.

Spinal cord tissue samples were collected 30 days post-disease induction, fixed in 4% paraformaldehyde, and dehydrated and embedded in paraffin. Spinal cord sections were cut at 6 µm and processed for histological analysis by staining with haematoxylin and eosin (H&E) to evaluate immune cell infiltration, and with luxol fast blue to mark the area of demyelination.

Blood samples were collected on day 30 post-immunization and serum was extracted for cytokine analysis. Cytokine levels were evaluated by Mouse Th1/Th2 cytokine kit-BD cytometric Bead Array (CBA) according to the manufacturer's instructions.

The effect of the BKT-P2-FC and BKT-P46-FC polypeptides was determined by monitoring the EAE clinical score in the animal subjects. Clinical scores for EAE were determined according to the following criteria: 0—no disease; 1—decreased tail tone; 2—hind limb weakness or partial paralysis; 3—complete hind limb paralysis; 4—front and hind limb paralysis; 5—moribund state. Accumulating scores were calculated by summing all results for all animals in an experimental group at the end of the experiment.

For all EAE experiments there were ten to twelve mice per group.

Example 1

Preparation of Polypeptides

The BKT-P2 peptide (SEQ ID NO: 101) and the BKT-P46 peptide (SEQ ID NO: 76) (referred to herein as "BKT peptides") were used as a basis for preparing polypeptides having a BKT peptide fused to the N'-terminus of secreted non-glycosylated human IgG1 Fc (Fc N297A).

To allow DNA cloning, the BKT-P2 and BKT-P46 peptide sequences were back-translated into DNA sequences. Each BKT peptide sequence was fused to the DNA sequence encoding the human IL6 signal peptide in order to allow protein secretion in a mammalian system. This procedure was performed by two-step PCR as described hereinabove. The IL6-BKT peptide DNA fragments obtained by PCR were then digested and ligated in-frame to a non-glycosylated Fc sequence (containing the point mutation N297A) to give fragments designated IL6-P2-Fc N297A (SEQ ID NO: 168) and IL6-P46-Fc N297A (SEQ ID NO: 169), using the procedures described hereinabove.

The IL6-BKT peptide-Fc DNA constructs were then transfected into HEK-293T cells using FuGENE® 6 transfection reagent. Each construct was transfected into two wells of a 6-well plate. One well was dedicated for Western blot (WB) analysis and the second well was dedicated for the establishment of a stable pool. The cells were plated in 6-wells plates at a concentration of 500,000 cells per well. A day later, the cells were transfected with 6 µl of FuGENE and 2 µg DNA (at a ratio of 3:1).

In wells dedicated for WB analysis, the medium was replaced after 24 hours with serum-free medium and the medium was collected 48 hours later. Transiently transfected cells were analyzed by Western blot analysis using anti-Fc antibodies, and were found to express the desired polypeptides, designated BKT-P2-FC (SEQ ID NO: 158) and BKT-P46-FC (SEQ ID NO: 159) (data not shown).

In the other wells, the medium was replaced after 24 hours with DMEM (Dulbecco's modified Eagle medium) containing 10% FCS (fetal calf serum), and 48 hours later, the cells were trypsinized and transferred to a T75 flask containing selection medium (DMEM with 10% FCS and 5 µg/ml puromycin) for obtaining stable clones.

The cell population which survived puromycin selection (the stable pool) was propagated, and the medium of the cell population was analyzed by Western blot analysis, as described hereinabove, in order to confirm expression of the desired polypeptide.

As shown in FIG. 2, the desired BKT-P2-FC and BKT-P46-FC polypeptides were expressed in all of the tested cell cultures.

In addition, supernatants from the abovementioned pools were tested by ELISA directed to an Fc fragment, and the results indicated expression of desired BKT-P2-FC or BKT-P46-FC polypeptide in all of the tested cultures (data not shown).

To verify the identity of cells, genomic PCR was performed, and the results indicated that the correct sequences integrated into the cell genome (data not shown).

Several aliquots of each pool expressing the desired polypeptides were cryopreserved at liquid nitrogen. Several days later, one ampoule from each stock was thawed, in order to confirm cell viability.

The BKT-P2-FC (SEQ ID NO: 158) and BKT-P46-FC (SEQ ID NO: 159) polypeptides were then produced in mammalian culture grown in suspension. One T175 flask of transfected cells was maintained in 10% serum supplemented medium, containing a selection antibiotic (5 µg/ml puromycin) and incubated in 5% $CO_2$ at 37° C. Following trypsinization, cells were transferred into serum-free medium (EX-CELL® 293 medium) supplemented with 4 mM glutamine and a selection antibiotic (1 µg/ml puromycin), and were further incubated in flasks in 5% $CO_2$ at 37° C. After three days, the cells were transferred to shake flasks at 37° C., with an agitation speed of 125 rotations per minute. When the cell density reached $2.0-3.5\times10^6$ cells per ml, the culture volume was increased by sequential dilutions up to 4 liters in two spinner flasks. One shake flask containing 200 ml of culture was kept as backup.

After a production phase of 4 days, the cultures of the two spinner flasks reached $3.7\times10^6$ cells per ml with 91% viability, and $4.0\times10^6$ cells per ml with 92% viability, respectively. Medium from the two spinner flasks and the 200 ml from the shake flask were harvested by centrifugation (5000 rotations per minute, 15 minutes). A total of 3.5 liters was collected, filtered through a 0.22 µm filter, and kept at −80° C. (two 1.5 ml samples were taken). The polypeptide (SEQ ID NO: 158 or SEQ ID NO: 159) was further purified on a protein A column.

Example 2

Affinity of Polypeptides to Chemokines

The affinity of the polypeptides described in Example 1 to chemokines was determined by Surface Plasmon Resonance (SPR), as described in the Materials and Methods section. The results are summarized in Table 3 below.

As shown in Table 3, the polypeptides bound to each of the chemokines I-TAC, IP-10, MIG, MCP-1, eotaxin and RANTES to an appreciable extent.

TABLE 3

Dissociation constants ($K_d$) for binding of polypeptides to chemokines

| Chemokine | BKT-P2-FC SEQ ID NO: 158 | | BKT-P46-FC SEQ ID NO: 159 | |
|---|---|---|---|---|
| | Dissociation constant ($K_d$) (M) | Chi$^2$ | Dissociation constant ($K_d$) (M) | Chi$^2$ |
| I-TAC | $8.3 \times 10^{-8}$ | 0.51 | $3.7 \times 10^{-7}$ | 0.76 |
| IP-10 | $3.8 \times 10^{-8}$ | 1.05 | $6.3 \times 10^{-9}$ | 0.99 |
| MIG | $1.3 \times 10^{-7}$ | 1.05 | $1.8 \times 10^{-8}$ | 0.61 |
| MCP-1 | $6.5 \times 10^{-6}$ | 0.65 | $4.6 \times 10^{-8}$ | 0.75 |
| Eotaxin | $2.7 \times 10^{-5}$ | 1.2 | $5 \times 10^{-6}$ | 0.51 |
| RANTES | $1.8 \times 10^{-8}$ | 0.6 | Not determined | Not determined |

Example 3

In Vitro Activity of Polypeptides

Using the in vitro adhesion assay described hereinabove, the effects of the chemokine binding peptides BKT-P2 (SEQ ID NO: 101) and BKT-P46 (SEQ ID NO: 76) on adhesion of T cells to VCAM-1 was compared with those of the polypeptides described in Example 1, which comprise one of the aforementioned chemokine binding peptide sequences. The ability of the aforementioned peptides and polypeptides to inhibit adhesion of T cells to VCAM-1 is summarized in Table 4 below.

TABLE 4

Inhibition of chemokine-dependent T cell adhesion by peptides

| Peptide (SEQ ID NO:) | Chemokine | | | | | | | | |
|---|---|---|---|---|---|---|---|---|---|
| | IP-10 | I-TAC | MIG | MCP-1 | RANTES | Eotaxin | SDF-1 | BCA-1 | IL-8 |
| BKT-P2 (101) | ++ | ++ | − | ++ | ++ | ++ | − | − | N.D. |
| BKT-P2-FC (158) | ++ | ++ | ++ | ++ | ++ | ++ | N.D. | N.D. | N.D. |
| BKT-P46 (76) | − | ++ | ++ | ++ | ++ | − | − | N.D. | − |
| BKT-P46-FC (159) | − | ++ | ++ | ++ | ++ | ++ | − | − | N.D. |

++ = 100% inhibition
− = no inhibition
N.D. = not determined

As shown in Table 4 and in FIGS. 3A, 3B and 3C, the peptide BKT-P2 inhibited T cell adhesion induced by IP-10, I-TAC, MCP-1, RANTES and eotaxin, but not adhesion induced by MIG.

As shown in Table 4 and in FIGS. 4A, 4B and 4C, the polypeptide BKT-P2-FC inhibited T cell adhesion induced by MIG, as well as adhesion induced by IP-10, I-TAC, MCP-1, RANTES and eotaxin.

As further shown in Table 4, the peptide BKT-P46 inhibited T cell adhesion induced by I-TAC, MIG, MCP-1 and RANTES, but not adhesion induced by eotaxin, whereas the polypeptide BKT-P46-FC inhibited T cell adhesion induced by eotaxin, as well as by I-TAC, MIG, MCP-1 and RANTES.

The above results indicate that the polypeptides have an enhanced ability to modulate chemokine activity as compared to the ability of the corresponding chemokine-binding peptides to modulate chemokine activity. This may be a result of prolonged lifetime and enhanced stability of the polypeptides relative to the peptides, and/or due to changes in their tertiary conformation.

Example 4

In Vivo Effect of Polypeptides on Experimental Autoimmune Encephalomyelitis (EAE)

The effect on brain inflammation of the BKT-P2-FC and BKT-P46-FC polypeptides described in Example 1 was tested and scored using an in vivo experimental autoimmune encephalomyelitis model, as described in the Materials and Methods section.

Figure 5A:
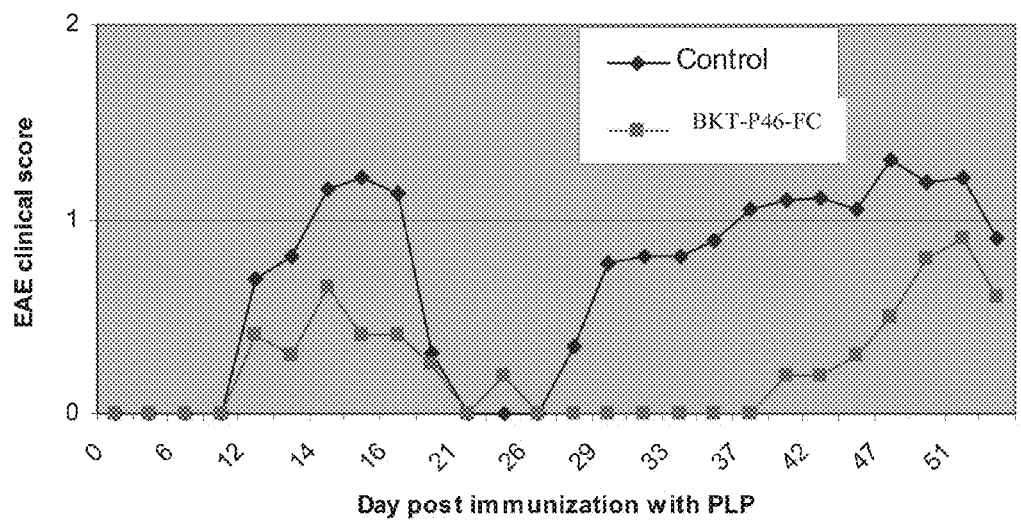
FIGS. 5A and 5B are graphs showing the average clinical score for EAE (experimental autoimmune encephalomyelitis) as a function of time following immunization with PLP (proteolipid protein) to induce acute disease (FIG. 5A) and the average accumulating clinical score (FIG. 5B) for EAE, in control mice and in mice treated with the exemplary polypeptide having SEQ ID NO: 159 (BKT-P46-FC)
Figure 5B:
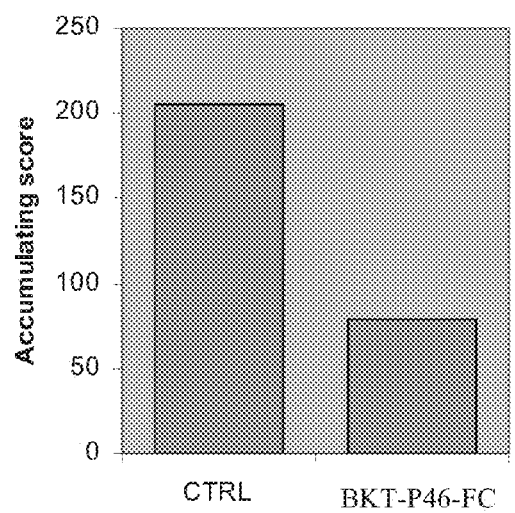

As shown in FIGS. 5A and 5B, the BKT-P46-FC polypeptide considerably decreased the average clinical score and accumulating clinical score of PLP-derived EAE for the duration of the experiment (through day 55).

On day 37 of the experiment, 6 of 13 control mice had EAE clinical scores of at least 2, whereas all 10 mice which received the BKT-P46-FC polypeptide had an EAE clinical score of 0.

Figure 6A:
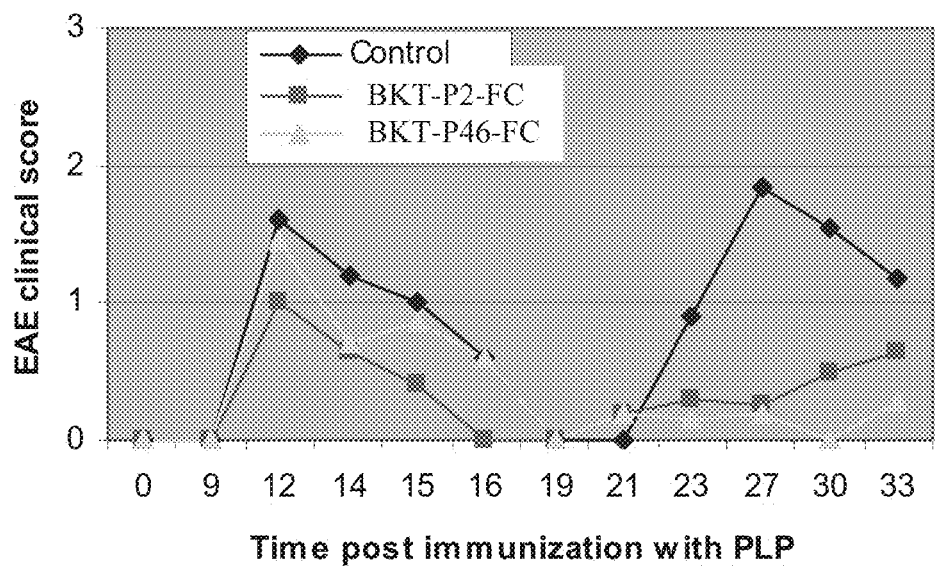
FIGS. 6A and 6B are graphs showing the average clinical score for EAE (experimental autoimmune encephalomyelitis) as a function of time following immunization with PLP (proteolipid protein) to induce acute disease (FIG. 6A) and the average accumulating clinical score (FIG. 6B) for EAE, in control mice and in mice treated with the exemplary polypeptides having SEQ ID NO: 159 (BKT-P46-FC) or SEQ ID NO: 158 (BKT-P2-FC)
Figure 6B:
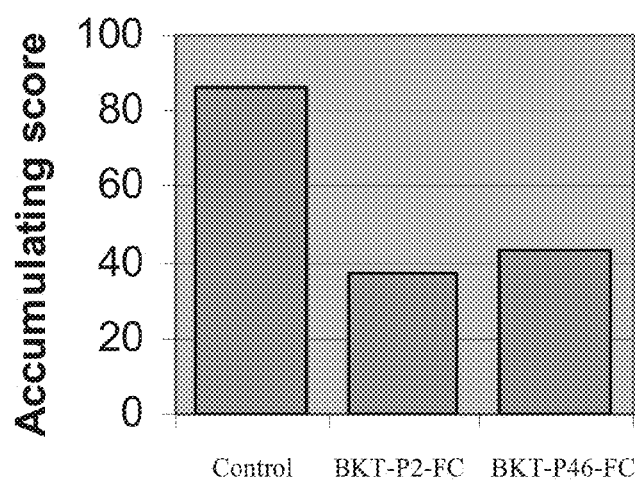

In addition, as shown in FIGS. 6A and 6B, both the BKT-P46-FC and BKT-P2-FC polypeptides decreased the average clinical score and accumulating clinical score of PLP-derived EAE for the duration of the experiment (through day 33).

On day 27 of the experiment, 8 of 10 control mice had EAE clinical scores of at least 2, whereas 9 of 10 mice which received the BKT-P2-FC polypeptide, and 8 of 10 mice which received the BKT-P46-FC polypeptide, had EAE clinical scores of 0.

Figure 7:
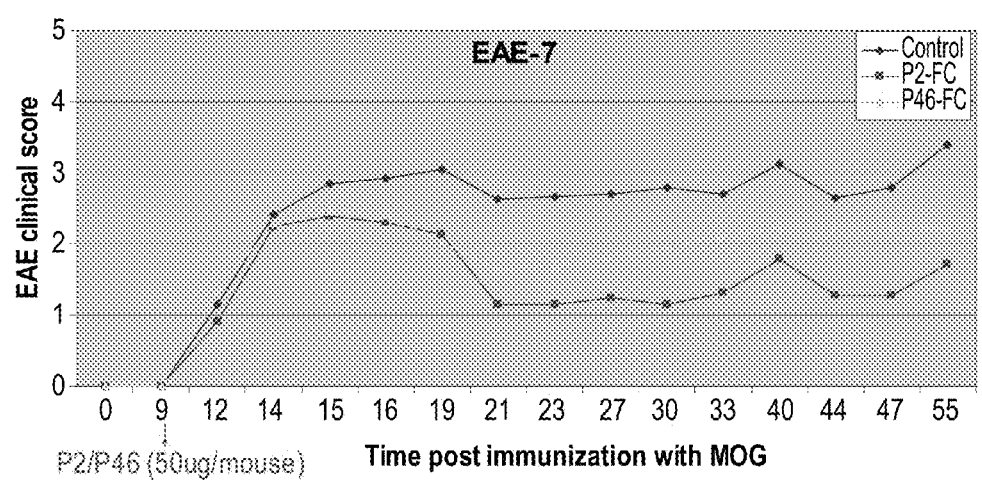
FIG. 7 is a graph showing the average clinical score for EAE (experimental autoimmune encephalomyelitis) as a function of time following immunization with MOG peptide to induce chronic disease, in control mice and in mice treated with the exemplary polypeptides having SEQ ID NO: 158 (BKT-P2-FC) or SEQ ID NO: 159 (BKT-P46-FC)

Similarly, as shown in FIG. 7, both the BKT-P46-FC and BKT-P2-FC polypeptides decreased the average clinical score of MOG-derived EAE for the duration of the experiment (through day 55).

These results indicate that the polypeptides are effective at inhibiting an inflammatory response in the brain of mice, such as that of EAE, a model of multiple sclerosis.

Example 5

In Vivo Effect of Polypeptides on Arthritis

The effect of the BKT-P2-FC polypeptide described in Example 1 on arthritis was tested using an in vivo mouse induced arthritis model. The assay was performed as described in Coelho et al. [*Arthritis Rheum* 2008, 58:2329-2337], Grespan et al. [*Arthritis Rheum* 2008, 58:2030-2040] and Lemos et al. [*PNAS* 2009, 106:5954-5959].

On day 0, the mice were immunized intradermally at the base of the tail with 500 µg of methylated bovine serum albumin (mBSA) in 100 µl of an emulsion of saline and an equal volume of Freund's complete adjuvant (CFA). On day 11, the BKT-P2-FC polypeptide was administered at a dose of 2 mg/kg. 24 hours later, an antigen challenge was performed in the mice. Each mouse received an injection of 10 µg of mBSA (in 10 µl sterile saline) in the left knee joint. 48 hours after administration of the polypeptide, the mice were killed, the knee cavity was washed with PBS, and the number of leukocytes in the tissue was determined by counting the leukocytes using fluorescence-activated cell sorting (FACS).

As shown in FIGS. 8A and 8B, the BKT-P2-FC polypeptide considerably reduced the number of neutrophils and the number of monocytes in the arthritic knee cavity.

These results indicate that the polypeptides are effective at inhibiting an inflammatory response, such as that of rheumatoid arthritis.

Example 6

In Vivo Effect of Polypeptides on Delayed Type Hypersensitivity (DTH)

The effect of the BKT-P2-FC and BKT-P46-FC polypeptides described in Example 1 on immune responses was further tested using an in vivo delayed type hypersensitivity mouse model.

The nice (8- to 10-week-old male C57BL/6 mice) were immunized intradermally at the base of the tail with 500 µg of methylated bovine serum albumin (mBSA) in 100 µl of an emulsion of saline and an equal volume of Freund's complete adjuvant on day 0. Twelve days later, an antigen challenge was performed in the mice. Each mouse received an injection of 10 µg of mBSA (in 10 µl sterile saline) in the left knee joint, as described in Coelho et al. [*Arthritis Rheum* 2008, 58:2329-2337] and Healy et al. [*J Immunol* 2006, 177:1886-1893]. In some mice, BKT-P2-FC (50 µg/mouse) was intravenously injected 24 hours before challenge. Naïve mice which were challenged with sham immunization of PBS were served as control mice. 24 hours after antigen challenge, the mice were killed.

As shown in FIG. 9, both of the abovementioned polypeptides inhibited delayed type hypersensitivity, with BKT-P2-FC being more potent than BKT-P46-FC.

These results indicate that the polypeptides are effective at inhibiting a delayed type hypersensitivity inflammatory response.

Example 7

Pharmacokinetics of Polypeptides

The pharmacokinetics of the polypeptides in mice was determined in C57BL/6 mice which were intravenously injected with 50 µg/mouse of BKT-P46-FC (SEQ ID NO: 159) or BKT-P2-FC (SEQ ID NO: 158) polypeptides.

The mice were bled 2 hours, 24 hours, 5 and 11 days post-injection, and serum was extracted. The level of polypeptides in the serum was tested using a Human total IgG ELISA kit (ICL) according to the manufacturer's instructions.

The polypeptides were detected in the blood even 11 days after injection.

These results indicate that the polypeptides have considerable stability in vivo.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

TABLE 5

Chemokine-binding peptides

| Chemokine-binding peptide name | SEQ ID NO: | Sequence of peptide |
|---|---|---|
| BKT-P50 | 1 | CAHLSPHKC |
| BKT-P10 | 2 | CDIPWRNEC |
| BKT-P17 | 3 | CDPLRQHSC |
| BKT-P58 | 4 | CDSLGHWLC |
| BKT-P15 | 5 | CDYTTRHSC |
| BKT-P59 | 6 | CHGTLNPEC |
| BKT-P56 | 7 | CHHNLSWEC |
| BKT-P60 | 8 | CHIWTLASC |
| BKT-P61 | 9 | CHNTFSPRC |
| BKT-P62 | 10 | CIPLHASLC |
| BKT-P63 | 11 | CITTTSLSC |
| BKT-P64 | 12 | CKLTTCKDC |
| BKT-P65 | 13 | CKNHTTFWC |
| BKT-P66 | 14 | CLKLLSRSC |
| BKT-P67 | 15 | CLLKAHPSC |
| BKT-P68 | 16 | CLNQLKQAC |
| BKT-P69 | 17 | CMNFPSPHC |
| BKT-P70 | 18 | CPQSPTYTC |
| BKT-P57 | 19 | CPSSAIHTC |
| BKT-P71 | 20 | CPTSTARIC |
| BKT-P72 | 21 | CQASSFPSC |
| BKT-P73 | 22 | CQPYFWYRC |
| BKT-P14 | 23 | CQTLTPSIC |
| BKT-P74 | 24 | CSKLGHLWC |
| BKT-P75 | 25 | CSKTPERIX |
| BKT-P76 | 26 | CSNNNRMTC |
| BKT-P77 | 27 | CSPILSLSC |
| BKT-P16 | 28 | CSPTNFTRC |
| BKT-P78 | 29 | CSRPAMNVC |
| BKT-P79 | 30 | CSTKAYPNC |
| BKT-P80 | 31 | CSTSSCGSC |
| BKT-P81 | 32 | CSYWGHRDC |
| BKT-P13 | 33 | CTAHDANAC |
| BKT-P82 | 34 | CTANSEKTC |
| BKT-P83 | 35 | CTHPKASMC |
| BKT-P84 | 36 | CTKTINGKC |
| BKT-P85 | 37 | CTNMQSPLC |
| BKT-P86 | 38 | CTPFTKLPC |
| BKT-P87 | 39 | CTPTTDSIC |
| BKT-P88 | 40 | CTQQNGHPC |
| BKT-P12 | 41 | ACTTPSKHQC |
| BKT-P89 | 42 | CTYNVAKPC |
| BKT-P90 | 43 | ACAPLMFSQC |
| BKT-P48 | 44 | ACHASLKHRC |

TABLE 5-continued

Chemokine-binding peptides

| Chemokine-binding peptide name | SEQ ID NO: | Sequence of peptide |
|---|---|---|
| BKT-P91 | 45 | AHFSPNLLLGG |
| BKT-P44 | 46 | AHSLKSITNHGL |
| BKT-P92 | 47 | AKTLMPSPFPRT |
| BKT-P93 | 48 | ASAVGSLSIRWQ/L/G |
| BKT-P94 | 49 | ASWVDSRQPSAA |
| BKT-P95 | 50 | CPQLTVGQHRT |
| BKT-P8 | 51 | DLPPTLHTTGSP |
| BKT-P96 | 52 | DSSNPIFWRPSS |
| BKT-P97 | 53 | EFLGVPASLVNP |
| BKT-P51 | 54 | ESDLTHALHWLG |
| BKT-P98 | 55 | EVHSTDRYRSIP |
| BKT-P99 | 56 | FGLQPTGDIARR |
| BKT-P9 | 57 | FSMDDPERVRSP |
| BKT-P100 | 58 | FSPLHTSTYRPS |
| BKT-P27 | 59 | GDFNSGHHTTTR |
| BKT-P28 | 60 | GPSNNLPWSNTP |
| BKT-P33 | 61 | GVHKHFYSRWLG |
| BKT-P101 | 62 | HAPLTRSPAPNL |
| BKT-P102 | 63 | HGSLTTLF/LRYEP |
| BKT-P45 | 64 | HHFHLPKLRPPV |
| BKT-P55 | 65 | HHTWDTRIWQAF |
| BKT-P54 | 66 | HPTTPFIHMPNF |
| BKT-P103 | 67 | HRDPXS(P)PSAA/GRP |
| BKT-P104 | 68 | HNVTTRTQRLMP |
| BKT-P49 | 69 | HSACHASLKHRC |
| BKT-P105 | 70 | HSACKLTTCKDG |
| BKT-P6 | 71 | HSACLSTKTNIC |
| BKT-P106 | 72 | IAHVPETRLAQM |
| BKT-P107 | 73 | IFSMGTALARPL |
| BKT-P108 | 74 | INKHPQQVSTLL |
| BKT-P7 | 75 | ISPSHSQAQADL |
| BKT-P46 | 76 | LDYPIPQTVLHH |
| BKT-21 | 77 | LFAAVPSTQFFR |
| BKT-P22/38 | 78 | LGFDPTSTRFYT |
| BKT-P37 | 79 | LLADTTHHRPWP |
| BKT-P109 | 80 | LPWAPNLDSTA |
| BKT-P110 | 81 | LQPSQPQRFAPT |
| BKT-P111 | 82 | LSPPMQLQPTYS |
| BKT-P112 | 83 | MHNVSDSNDSAI |
| BKT-P113 | 84 | NSSMLGMLPSSF |
| BKT-P114 | 85 | NTSSSQGTQRLG |
| BKT-P42 | 86 | PGQWPSSLTLYK |
| BKT-P23 | 87 | QIPQMRILHPYG |
| BKT-P24 | 88 | QIQKPPRTPPSL |
| BKT-P115 | 89 | QLTQTMWKDTTL |
| BKT-P116 | 90 | QNLPPERYSEAT |
| BKT-P117 | 91 | QSLSFAGPPAWQ |
| BKT-P118 | 92 | QTTMTPLWPSFS |
| BKT-P119 | 93 | RCMSEVISFNCP |
| BKT-P120 | 94 | RSPYYNKWSSKF |
| BKT-P39 | 95 | SAGHIHEAHRPL |
| BKT-P40 | 96 | SAISDHRAHRSH |
| BKT-P121 | 97 | SEPTYWRPNMSG |
| BKT-P32 | 98 | SFAPDIKYPVPS |
| BKT-P31 | 99 | SFWHHHSPRSPL |
| BKT-P3 | 100 | SIFAHQTPTHKN |
| BKT-P2 | 101 | SIPSHSIHSAKA |
| BKT-P122 | 102 | SIRTSMNPPNLL |
| BKT-P123 | 103 | SLPHYIDNPFRQ |
| BKT-P29 | 104 | SLSKANILHLYG |
| BKT-P124 | 105 | SLVTADASFTPS |
| BKT-P125 | 106 | SMVYGNRLPSAL |
| BKT-P126 | 107 | SPSLMARSSPYW |
| BKT-P127 | 108 | SPNLPWSKLSAY |
| BKT-P1 | 109 | SQTLPYSNAPSP |
| BKT-P128 | 110 | SSTQAHPFAPQL |
| BKT-P129 | 111 | STPNSYSLPQAR |
| BKT-P4 | 112 | STVVMQPPPRPA |
| BKT-P34 | 113 | SVQTRPLFHSHF |
| BKT-P130 | 114 | SVSVGMKPSPRP |
| BKT-P131 | 115 | SYIDSMVPSTQT |
| BKT-P132 | 116 | SYKTTDSDTSPL |
| BKT-P133 | 117 | TAAASNLRAVPP |
| BKT-P5 | 118 | TAPLSHPPRPGA |

TABLE 5-continued

Chemokine-binding peptides

| Chemokine-binding peptide name | SEQ ID NO: | Sequence of peptide |
|---|---|---|
| BKT-P134 | 119 | TGLLPNSSGAGI |
| BKT-P135 | 120 | TGPPSRQPAPLH |
| BKT-P30 | 121 | TLSNGHRYLELL |
| BKT-P25 | 122 | TPSPKLLQVFQA |
| BKT-P136 | 123 | TPSTGLGMSPAV |
| BKT-P137 | 124 | TPVYSLKLGPWP |
| BKT-P47 | 125 | TRLVPSRYYHHP |
| BKT-P138 | 126 | TSPIPQMRTVPP |
| BKT-P139 | 127 | TTNSSMTMQLQR |
| BKT-P140 | 128 | TTTLPVQPTLRN |
| BKT-P141 | 129 | TTTWTTTARWPL |
| BKT-P142 | 130 | TVAQMPPHWQLT |
| BKT-P143 | 131 | TWNSNSTQYGNR |
| BKT-P144 | 132 | TWTLPAMHPRPA |
| BKT-P26 | 133 | VHTSLLQKHPLP |
| BKT-P35 | 134 | VLPNIYMTLSA |
| BKT-P145 | 135 | VMDFASPAHVLP |
| BKT-P146 | 136 | VNQEYWFFPRRP |
| BKT-P147 | 137 | VYSSPLSQLPR |
| BKT-P148 | 138 | VPPIS(R)TFLF(L)ST(K)S |
| BKT-P149 | 139 | VPPLHPALSRXN |
| BKT-P43 | 140 | VSPFLSPTPLLF |
| BKT-P150 | 141 | VSRLGTPSMHPS |
| BKT-P151 | 142 | WPFNHFPWWNVP |
| BKT-P52 | 143 | WSAHIVPYSHKP |
| BKT-P152 | 144 | WWPNSLNWVPRP |
| BKT-P53 | 145 | YATQHNWRLKHE |
| BKT-P153 | 146 | YCPMRLCTDC |
| BKT-P154 | 149 | YGKGFSPYFHVT |
| BKT-P155 | 148 | YPHYSLPGSSTL |
| BKT-P156 | 149 | YPSLLKMPQPFS |
| BKT-P157 | 150 | YQPRPFVTTSPM |
| BKT-P158 | 151 | YSAPLARSNVVM |
| BKT-P36 | 152 | YTRLSHNPYTLS |
| BKT-P41 | 153 | YTTHVLPFAPSS |
| BKT-P159 | 154 | YTWQTIREQYEM |
| BKT-P6 | 155 | CLSTKTNIC |
| BKT-P16 | 156 | ACLSTKTNIC |
| BKT-P11 | 157 | CTTPSKHQC |

What is claimed is:

1. A method of treating inflammation or an autoimmune disease in a subject in need thereof, the method comprising administering to the subject an isolated polypeptide as set forth in SEQ ID NO: 159, thereby treating the inflammation or said autoimmune disease.

2. The method of claim 1, wherein said inflammation is selected from the group consisting of delayed type hypersensitivity, rheumatoid arthritis, multiple sclerosis, colitis, psoriasis, atherosclerosis, hypertension, and myasthenia gravis.

* * * * *